(12) United States Patent
Slocum et al.

(10) Patent No.: US 12,070,256 B2
(45) Date of Patent: *Aug. 27, 2024

(54) BI-SPRING SURGICAL IMPACT TOOL

(71) Applicant: Zimmer, Inc., Warsaw, IN (US)

(72) Inventors: Alexander Slocum, Bow, NH (US); Nicholas Oblas, Warsaw, IN (US); Tom O'Donnell, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 390 days.

This patent is subject to a terminal disclaimer.

(21) Appl. No.: 17/523,540

(22) Filed: Nov. 10, 2021

(65) Prior Publication Data

US 2022/0142693 A1     May 12, 2022

Related U.S. Application Data

(60) Provisional application No. 63/111,789, filed on Nov. 10, 2020.

(51) Int. Cl.
*A61B 17/92* (2006.01)
*A61F 2/46* (2006.01)

(52) U.S. Cl.
CPC .............. *A61B 17/92* (2013.01); *A61F 2/46* (2013.01); *A61B 2017/925* (2013.01); *A61B 2017/928* (2013.01); *A61F 2002/4681* (2013.01)

(58) Field of Classification Search
CPC ............... A61B 17/92; A61B 17/921; A61B 2017/922; A61B 2017/924;
(Continued)

(56) References Cited

U.S. PATENT DOCUMENTS

| 974,267 A | 11/1910 | Hennessy et al. |
| 2,542,695 A | 2/1951 | Neff et al. |
| (Continued) | | |

FOREIGN PATENT DOCUMENTS

| AU | 2019203142 A1 | 11/2019 |
| AU | 2020200771 A1 | 2/2020 |
| (Continued) | | |

OTHER PUBLICATIONS

"International Application Serial No. PCT/US2021/058776, International Search Report mailed Feb. 9, 2022", 5 pgs.
(Continued)

*Primary Examiner* — Jessica Weiss
(74) *Attorney, Agent, or Firm* — SCHWEGMAN LUNDBERG & WOESSNER, P.A.

(57) ABSTRACT

Disclosed herein are bi-spring surgical impact tools and methods of use thereof. The bi-spring surgical impact tools can include a housing, a shuttle, a pinion, and first and second springs. The housing can define a cavity having a first end and a second end. The shuttle can be located within the cavity and define a plurality of indentations. The pinion can be located proximate the shuttle and have a plurality of protrusions sized to mesh with the plurality of indentations during rotation of the pinion. The first and second springs can be mechanically coupled to the housing and the shuttle. Rotation of the pinion in a first direction can translate the shuttle in a first direction towards the first end of the housing and rotation of the pinion in a second direction can translate the shuttle in a second direction towards the second end of the housing.

20 Claims, 21 Drawing Sheets

(58) Field of Classification Search
CPC ........ A61B 2017/925; A61B 2017/927; A61B 2017/928; A61F 2/46; A61F 2002/4681
See application file for complete search history.

(56) References Cited

U.S. PATENT DOCUMENTS

| | | | |
|---|---|---|---|
| 2,576,851 A * | 11/1951 | Newman | B25B 23/1405 |
| | | | 134/169 R |
| 2,655,921 A | 10/1953 | Haboush | |
| 3,450,215 A | 6/1969 | Emery | |
| 3,472,323 A | 10/1969 | Hall | |
| 3,626,935 A | 12/1971 | Pollock et al. | |
| 3,752,161 A | 8/1973 | Bent | |
| 4,298,074 A | 11/1981 | Mattchen | |
| 4,466,429 A | 8/1984 | Loscher et al. | |
| 4,651,833 A | 3/1987 | Karpf et al. | |
| 4,834,092 A | 5/1989 | Alexson et al. | |
| 5,057,112 A | 10/1991 | Sherman et al. | |
| 5,108,400 A | 4/1992 | Appel et al. | |
| 5,152,352 A | 10/1992 | Mandanis | |
| 5,163,519 A | 11/1992 | Mead et al. | |
| 5,210,918 A | 5/1993 | Wozniak et al. | |
| 5,282,805 A | 2/1994 | Richelsoph et al. | |
| 5,352,230 A | 10/1994 | Hood | |
| 5,353,230 A | 10/1994 | Maejima et al. | |
| 5,363,726 A * | 11/1994 | Smith | B25B 17/00 |
| | | | 81/57.29 |
| 5,431,660 A | 7/1995 | Burke | |
| 5,485,887 A | 1/1996 | Mandanis | |
| 5,553,675 A | 9/1996 | Pitzen et al. | |
| 6,126,694 A | 10/2000 | Gray, Jr. | |
| 6,159,214 A | 12/2000 | Michelson | |
| 6,264,660 B1 | 7/2001 | Schmidt et al. | |
| 6,264,661 B1 | 7/2001 | Jerger et al. | |
| 6,368,324 B1 | 4/2002 | Dinger | |
| 6,520,266 B2 | 2/2003 | Bongers-Ambrosius et al. | |
| 6,626,913 B1 | 9/2003 | Mckinnon et al. | |
| 6,814,738 B2 | 11/2004 | Naughton et al. | |
| 6,868,918 B2 | 3/2005 | Shinohara | |
| 7,090,677 B2 | 8/2006 | Fallin et al. | |
| 7,189,241 B2 | 3/2007 | Yoon et al. | |
| 7,637,327 B2 | 12/2009 | Gruenig | |
| 8,002,776 B2 | 8/2011 | Liu et al. | |
| 8,393,409 B2 | 3/2013 | Pedicini | |
| 8,444,647 B2 | 5/2013 | Walen et al. | |
| 8,465,492 B2 | 6/2013 | Estes | |
| 8,556,901 B2 | 10/2013 | Anthony et al. | |
| 8,602,124 B2 | 12/2013 | Pedicini | |
| 8,695,726 B2 * | 4/2014 | Pedicini | A61B 17/1628 |
| | | | 173/132 |
| 8,894,654 B2 | 11/2014 | Anderson | |
| 8,936,105 B2 | 1/2015 | Pedicini | |
| 8,936,106 B2 | 1/2015 | Pedicini | |
| 9,168,154 B2 | 10/2015 | Behzadi | |
| 9,186,158 B2 | 11/2015 | Anthony et al. | |
| 9,198,675 B2 | 12/2015 | Nelson et al. | |
| 9,220,612 B2 | 12/2015 | Behzadi | |
| 9,554,965 B2 | 1/2017 | Foehrenbach | |
| 9,629,641 B2 | 4/2017 | Ferro et al. | |
| 9,649,202 B2 | 5/2017 | Behzadi et al. | |
| 9,877,734 B2 | 1/2018 | Anderson | |
| 9,901,354 B2 | 2/2018 | Pedicini | |
| 9,931,151 B2 | 4/2018 | Donald et al. | |
| 9,943,318 B2 | 4/2018 | Anthony et al. | |
| RE46,954 E | 7/2018 | Pedicini | |
| 10,028,754 B2 | 7/2018 | Johnson et al. | |
| RE46,979 E | 8/2018 | Pedicini | |
| 10,159,500 B2 | 12/2018 | Chavarria et al. | |
| 10,172,722 B2 | 1/2019 | Behzadi et al. | |
| 10,245,160 B2 | 4/2019 | Behzadi | |
| 10,245,162 B2 | 4/2019 | Behzadi et al. | |
| 10,251,663 B2 | 4/2019 | Behzadi | |
| 10,299,930 B2 | 5/2019 | Behzadi | |
| 10,342,591 B2 | 7/2019 | Pedicini | |
| 10,368,882 B2 | 8/2019 | Ferro et al. | |
| 10,413,425 B2 | 9/2019 | Behzadi et al. | |
| 10,426,540 B2 | 10/2019 | Behzadi | |
| 10,441,244 B2 | 10/2019 | Behzadi | |
| 10,456,271 B2 | 10/2019 | Behzadi | |
| 10,463,505 B2 | 11/2019 | Behzadi | |
| 10,470,897 B2 | 11/2019 | Behzadi | |
| 10,478,318 B2 | 11/2019 | Behzadi et al. | |
| 10,568,643 B2 | 2/2020 | Johnson et al. | |
| 10,603,173 B2 | 3/2020 | Carr et al. | |
| RE47,963 E | 4/2020 | Pedicini | |
| 10,610,379 B2 | 4/2020 | Behzadi | |
| RE47,997 E | 5/2020 | Pedicini | |
| 10,653,533 B2 | 5/2020 | Behzadi et al. | |
| 10,660,767 B2 | 5/2020 | Behzadi | |
| 10,729,559 B2 | 8/2020 | Behzadi et al. | |
| RE48,184 E | 9/2020 | Pedicini | |
| RE48,251 E | 10/2020 | Pedicini | |
| 11,013,503 B2 * | 5/2021 | Pedicini | A61F 2/4607 |
| 11,490,943 B2 | 11/2022 | Haiat et al. | |
| 11,918,268 B2 | 3/2024 | Doyle | |
| 11,925,359 B2 | 3/2024 | Slocum et al. | |
| 12,004,793 B2 | 6/2024 | Levy | |
| 2007/0282345 A1 * | 12/2007 | Yedlicka | A61B 17/1615 |
| | | | 606/80 |
| 2010/0137760 A1 | 6/2010 | Schulz et al. | |
| 2011/0255927 A1 * | 10/2011 | Boudreau | B23D 51/16 |
| | | | 279/144 |
| 2011/0270256 A1 | 11/2011 | Nelson et al. | |
| 2012/0172939 A1 * | 7/2012 | Pedicini | A61B 17/1604 |
| | | | 606/86 R |
| 2012/0215267 A1 | 8/2012 | Pedicini | |
| 2012/0259339 A1 | 10/2012 | Hood et al. | |
| 2013/0161050 A1 | 6/2013 | Pedicini | |
| 2013/0261681 A1 | 10/2013 | Bittenson | |
| 2014/0318819 A1 | 10/2014 | Pedicini | |
| 2014/0318823 A1 | 10/2014 | Pedicini | |
| 2015/0196343 A1 | 7/2015 | Donald et al. | |
| 2016/0199199 A1 | 7/2016 | Pedicini | |
| 2017/0020536 A1 | 1/2017 | Johnson et al. | |
| 2017/0056205 A1 | 3/2017 | Biegun et al. | |
| 2018/0055518 A1 * | 3/2018 | Pedicini | A61B 17/17 |
| 2018/0055552 A1 * | 3/2018 | Pedicini | A61B 17/92 |
| 2018/0303496 A1 | 10/2018 | Johnson et al. | |
| 2018/0318089 A1 | 11/2018 | Carr et al. | |
| 2018/0360464 A1 | 12/2018 | Irvine | |
| 2019/0167434 A1 | 6/2019 | Satterthwaite et al. | |
| 2019/0183554 A1 | 6/2019 | Pedicini | |
| 2019/0216521 A1 | 7/2019 | Chhatrala | |
| 2019/0247057 A1 | 8/2019 | Anderson | |
| 2019/0282286 A1 | 9/2019 | Pedicini | |
| 2022/0142693 A1 * | 5/2022 | Slocum | A61F 2/46 |
| 2022/0226033 A1 | 7/2022 | Slocum et al. | |
| 2022/0240946 A1 | 8/2022 | Slocum et al. | |
| 2022/0240947 A1 | 8/2022 | Marinkovich | |
| 2022/0240998 A1 * | 8/2022 | Slocum | A61B 17/92 |
| 2022/0273317 A1 * | 9/2022 | Levy | A61B 17/1624 |
| 2023/0240735 A1 | 8/2023 | Doyle | |
| 2024/0024012 A1 | 1/2024 | Dittrich et al. | |

FOREIGN PATENT DOCUMENTS

| | | |
|---|---|---|
| AU | 2017320580 B2 | 4/2023 |
| AU | 2021378282 A1 | 6/2023 |
| AU | 2022227599 A1 | 8/2023 |
| CA | 3063569 A1 | 11/2018 |
| CA | 3209081 A1 | 8/2022 |
| CA | 3211071 A1 | 9/2022 |
| CH | 701397 A2 | 1/2011 |
| CN | 2423872 Y | 3/2001 |
| CN | 204863450 U | 12/2015 |
| CN | 109070324 A | 12/2018 |
| CN | 108602180 B | 12/2022 |
| CN | 116801840 A | 9/2023 |
| CN | 117414174 A | 1/2024 |
| DE | 102010017726 A1 | 1/2011 |
| EP | 0290375 A1 | 11/1988 |
| FR | 2054809 A5 | 5/1971 |
| JP | H06229427 | 8/1994 |
| JP | 2002144255 | 5/2002 |

(56) References Cited

FOREIGN PATENT DOCUMENTS

| | | |
|---|---|---|
| JP | 2005506211 | 3/2005 |
| JP | 2010524577 | 7/2010 |
| JP | 2013036488 | 2/2013 |
| JP | 2015517341 | 6/2015 |
| JP | 2016202560 | 12/2016 |
| JP | 2018502689 | 2/2018 |
| JP | 2019524165 | 9/2019 |
| JP | 2019198645 | 11/2019 |
| JP | 2020185421 | 11/2020 |
| JP | 7127068 B2 | 8/2022 |
| JP | 2022166207 A | 11/2022 |
| JP | 7366968 B2 | 10/2023 |
| JP | 7375104 B2 | 10/2023 |
| JP | 7404463 B2 | 12/2023 |
| JP | 2023551117 A | 12/2023 |
| JP | 2024013234 A | 1/2024 |
| JP | 2024504977 A | 2/2024 |
| JP | 2024505231 A | 2/2024 |
| JP | 2024505239 A | 2/2024 |
| JP | 2024505543 A | 2/2024 |
| JP | 2024507954 A | 2/2024 |
| WO | WO-8802246 A2 | 4/1988 |
| WO | WO-8906516 A1 | 7/1989 |
| WO | WO-2008130904 A2 | 10/2008 |
| WO | WO-2016112397 A1 | 7/2016 |
| WO | WO-2018044348 A1 | 3/2018 |
| WO | WO-2018217250 A1 | 11/2018 |
| WO | WO-2022103835 A1 | 5/2022 |
| WO | WO-2022159704 A1 | 7/2022 |
| WO | WO-2022165215 A1 | 8/2022 |
| WO | WO-2022165223 A1 | 8/2022 |
| WO | WO-2022165357 A1 | 8/2022 |
| WO | WO-2022182772 A1 | 9/2022 |

OTHER PUBLICATIONS

"International Application Serial No. PCT/US2021/058776, Written Opinion mailed Feb. 9, 2022", 8 pgs.
"International Application Serial No. PCT/US2022/013312, International Search Report mailed Jun. 24, 2022", 6 pgs.
"International Application Serial No. PCT/US2022/013312, Invitation to Pay Additional Fees mailed May 3, 2022", 5 pgs.
"International Application Serial No. PCT/US2022/013312, Written Opinion mailed Jun. 24, 2022", 10 pgs.
"International Application Serial No. PCT/US2022/014368, International Search Report mailed May 30, 2022", 7 pgs.
"International Application Serial No. PCT/US2022/014368, Invitation to Pay Additional Fees mailed Apr. 5, 2022", 10 pgs.
"International Application Serial No. PCT/US2022/014368, Written Opinion mailed May 30, 2022", 8 pgs.
"International Application Serial No. PCT/US2022/014380, International Search Report mailed Jun. 24, 2022", 6 pgs.
"International Application Serial No. PCT/US2022/014380, Invitation to Pay Additional Fees mailed May 3, 2022", 5 pgs.
"International Application Serial No. PCT/US2022/014380, Written Opinion mailed Jun. 24, 2022", 7 pgs.
"International Application Serial No. PCT/US2022/014596, International Search Report mailed May 10, 2022", 4 pgs.
"International Application Serial No. PCT/US2022/014596, Written Opinion mailed May 10, 2022", 5 pgs.
"International Application Serial No. PCT/US2022/017537, International Search Report mailed Jun. 1, 2022", 4 pgs.
"International Application Serial No. PCT/US2022/017537, Written Opinion mailed Jun. 1, 2022", 5 pgs.
Budimir, Miles, "What is a rack and roller pinion?", [Online]. Retrieved from the Internet: <https://www.motioncontroltips.com/rack-roller-pinion/>, (Nov. 10, 2017), 13 pages.
Nexen, "Rack and Roller Pinion System", [Online]. Retrieved from the Internet: <https://www.nexengroup.com/nxn/products/prod-nav/lp/Roller+Pinion+System>, (Accessed online Apr. 27, 2021), 10 pages.

U.S. Appl. No. 18/222,830, filed Jul. 17, 2023, Linear Electric Surgical Hammer Impact Tool.
"U.S. Appl. No. 17/587,794, Response filed Aug. 28, 2023 to Restriction Requirement mailed Jun. 27, 2023", 7 pgs.
"U.S. Appl. No. 17/587,794, Restriction Requirement mailed Jun. 27, 2023", 7 pgs.
"International Application Serial No. PCT/US2021/058776, International Preliminary Report on Patentability mailed May 25, 2023", 10 pgs.
"International Application Serial No. PCT/US2022/013312, International Preliminary Report on Patentability mailed Aug. 3, 2023", 12 pgs.
"International Application Serial No. PCT/US2022/014368, International Preliminary Report on Patentability mailed Aug. 10, 2023", 10 pgs.
"International Application Serial No. PCT/US2022/014380, International Preliminary Report on Patentability mailed Aug. 10, 2023", 9 pgs.
"International Application Serial No. PCT/US2022/014596, International Preliminary Report on Patentability mailed Aug. 10, 2023", 7 pgs.
"International Application Serial No. PCT/US2022/017537, International Preliminary Report on Patentability mailed Sep. 7, 2023", 7 pgs.
"U.S. Appl. No. 17/587,794, Notice of Allowance mailed Nov. 15, 2023", 10 pgs.
"U.S. Appl. No. 17/678,807, Notice of Allowance mailed Feb. 14, 2024", 16 pgs.
"Australian Application Serial No. 2021378282, First Examination Report mailed Mar. 7, 2024", 3 pgs.
"European Application Serial No. 21820393.3, Response Filed Dec. 14, 2023 to Communication pursuant to Rules 161(1) and 162 EPC mailed Jul. 6, 2023", 10 pgs.
"European Application Serial No. 23186404.2, Extended European Search Report mailed Nov. 23, 2023", 8 pgs.
U.S. Appl. No. 17/581,316, filed Jan. 21, 2022, Linear Electric Surgical Hammer Impact Tool.
U.S. Appl. No. 17/587,794, filed Jan. 28, 2022, Rotary Electric Surgical Hammer Impact Tool.
U.S. Appl. No. 17/587,866, filed Jan. 28, 2022, Orthopedic Impactor Tool.
U.S. Appl. No. 17/589,456, filed Jan. 31, 2022, Tri-Roll Thread Electric Surgical Impact Tool.
U.S. Appl. No. 17/678,807, filed Feb. 23, 2022, Bi-Spring Surgical Hammer Impact Tools.
U.S. Appl. No. 18/593,177, filed Mar. 1, 2024, Chuck System for a Powered Surgical Impactor.
"U.S. Appl. No. 17/587,866, Notice of Allowance mailed Apr. 11, 2024", 17 pgs.
"Australian Application Serial No. 2023206091, First Examination Report mailed Apr. 19, 2024", 4 pgs.
"Australian Application Serial No. 2022211325, First Examination Report mailed Apr. 29, 2024", 3 pgs.
"Australian Application Serial No. 2022212126, First Examination Report mailed Apr. 26, 2024", 3 pgs.
"Australian Application Serial No. 2022227599, First Examination Report mailed Apr. 18, 2024", 2 pgs.
"Japanese Application Serial No. 2023-527766, Notification of Reasons for Refusal mailed Apr. 16, 2024", w English translation, 6 pgs.
"Japanese Application Serial No. 2023-546333, Notification of Reasons for Refusal mailed Apr. 16, 2024", w English translation, 8 pgs.
"Japanese Application Serial No. 2023-546135, Notification of Reasons for Refusal mailed Apr. 16, 2024", w English Translation, 9 pgs.
"Japanese Application Serial No. 2023-546065, Notification of Reasons for Refusal mailed Apr. 16, 2024", 15 pgs.
"Australian Application Serial No. 2022214931, First Examination Report mailed May 7, 2024", 3 pgs.
"Japanese Application Serial No. 2023-544157, Notice of Reasons for Rejection mailed Apr. 23, 2024", w English translation, 5 pgs.

(56) References Cited

OTHER PUBLICATIONS

"Australian Application Serial No. 2021378282, Response filed May 22, 2024 to First Examination Report mailed Mar. 7, 2024", 8 pgs.
"European Application Serial No. 22703776.9, Response Filed Mar. 11, 2024 to Communication pursuant to Rules 161(1) and 162 EPC mailed Aug. 30, 2023", 9 pgs.
"Australian Application Serial No. 2022212275, First Examination Report mailed May 15, 2024", 2 pgs.
"Australian Application Serial No. 2022212275, Response Filed Jun. 19, 2024 to First Examination Report mailed May 15, 2024", 14 pgs.
"Japanese Application Serial No. 2023-117628, Notification of Reasons for Refusal mailed May 28, 2024", w English translation, 7 pgs.

\* cited by examiner

BI-SPRING SURGICAL IMPACT TOOL

PRIORITY CLAIM

The present application claims priority to U.S. Provisional Application No. 63/111,789, entitled "BI-SPRING POWER IMPACT TOOL," filed on Nov. 10, 2020; the contents of which are hereby incorporated by reference in their entirety.

FIELD OF THE DISCLOSURE

The present disclosure relates generally to surgical instruments and use thereof. More specifically, the present disclosure relates to a bi-spring surgical impact tool and methods of use thereof.

BACKGROUND

Orthopedic surgeons commonly utilize tools for cutting or carving bone that require a hammer or mallet to transmit an impaction force to the tool. An example is a broach tool used to prepare the proximal end of a femur to receive the stem of a hip implant. Such broaches can be used with a hammer wielded by the physician or with a pneumatic "jackhammer'" like tool. However, striking a broach tool with a hammer can be tiresome and can cause high stresses on the physician's own joints, such as the shoulder joint. Furthermore, pneumatic impact tools require connection to an air hose, which can be inconvenient and can potentially limit the physician's ability to orient the tool in the desired manner.

SUMMARY

The following, non-limiting examples, detail certain aspects of the present subject matter to solve the challenges and provide the benefits discussed herein, among others.

Example 1 is a bi-spring surgical impact tool comprising: a housing defining a cavity having a first end and a second end; a shuttle located within the cavity and defining a plurality of indentations, the shuttle having a first end and a second end; a pinion located proximate the shuttle and having a plurality of protrusions sized to mesh with the plurality of indentations during rotation of the pinion; a first spring mechanically coupling the first end of the housing to the first end of the shuttle; and a second spring mechanically coupling the second end of the housing to the second end of the shuttle, wherein rotation of the pinion in a first rotational direction translates the shuttle in a first linear direction towards the first end of the housing and rotation of the pinion in a second rotational direction translates the shuttle in a second linear direction towards the second end of the housing.

In Example 2, the subject matter of Example 1 optionally includes wherein the pinion comprises: a pinion carriage; and a plurality of bearings that form the plurality of protrusions.

In Example 3, the subject matter of Example 2 optionally includes wherein the pinion carriage comprises a pinion plate defining a plurality of spokes, each of the plurality of bearings connected to a respective spoke of the pinion plate.

In Example 4, the subject matter of any one or more of Examples 2-3 optionally include wherein the pinion carriage comprises first and second pinion plates defining a plurality of spokes, each of the plurality of bearings located in between respective spokes of the first and second pinion plates.

In Example 5, the subject matter of any one or more of Examples 1-4 optionally include a drive rod oriented along an axis of the housing extending from the first end of the housing to the second end of the housing, the shuttle translatable along the drive rod, the shuttle and drive rod movable in the first and second linear directions along the axis of the housing.

In Example 6, the subject matter of Example 5 optionally includes wherein the first and second springs are located axially along a longitudinal axis of the drive rod.

In Example 7, the subject matter of any one or more of Examples 5-6 optionally include a drive rod collar affixed to the drive rod; and an insert coupled to the first spring and arranged to impact the drive rod collar upon disengagement of the plurality of protrusions from the plurality of the indentations.

In Example 8, the subject matter of any one or more of Examples 1-7 optionally include a motor; a switch; and a sensor arranged to detect a position of the shuttle and in electrical communication with the switch, wherein when the shuttle is out of position to allow the plurality of indentations of the shuttle to mesh with the plurality of the protrusions of the pinion, the switch severs electrical communication of the motor to a power supply.

In Example 9, the subject matter of any one or more of Examples 6-8 optionally include wherein the sensor is a Hall effect sensor.

In Example 10, the subject matter of any one or more of Examples 1-9 optionally include a chuck mechanically coupled to the shuttle.

Example 11 is a bi-spring surgical impact tool comprising: a housing defining a cavity having a housing axis that extends from a first end of the housing to a second end of the housing; a drive rod having a drive rod axis oriented parallel to the housing axis; a drive rod collar connected to the drive rod; a shuttle translatable along the drive rod and having a plurality of shuttle teeth; a pinion located proximate the shuttle and having a plurality of pinion teeth sized to mesh with the plurality of shuttle teeth; a first spring mechanically coupling the first end of the housing to the first end of the shuttle, the first spring located coaxially with the drive rod; and a second spring mechanically coupling the second end of the housing to the second end of the shuttle, the second spring located coaxially with the drive rod, wherein rotation of the pinion in a first rotational direction translates the shuttle in a first direction towards the first end of the housing and rotation of the pinion in a second rotational direction translates the shuttle in a second direction towards the second end of the housing, wherein when the shuttle is out of position to allow the plurality of shuttle teeth to mesh with the plurality of pinion teeth, the shuttle is movable by the first and second springs.

In Example 12, the subject matter of Example 11 optionally includes wherein the pinion comprises: a pinion carriage; and a plurality of bearings that form the teeth.

In Example 13, the subject matter of Example 12 optionally includes wherein the pinion carriage comprises a pinion plate defining a plurality of spokes, each of the plurality of bearings connected to a respective spoke of the pinion plate.

In Example 14, the subject matter of any one or more of Examples 12-13 optionally include wherein the pinion carriage comprises first and second pinion plates defining a plurality of spokes, each of the plurality of bearings located in between respective spokes of the first and second pinion plates.

In Example 15, the subject matter of any one or more of Examples 11-14 optionally include a motor; a switch; and a sensor arranged to detect a position of the shuttle and in electrical communication with the switch, wherein when the shuttle is out of position to allow the plurality of shuttle teeth to mesh with the plurality of pinion teeth, the switch severs electrical communication of the motor to a power supply.

Example 16 is a bi-spring surgical impact tool comprising: a housing defining a cavity having a housing axis that extends from a first end of the housing to a second end of the housing; a drive rod having a drive rod axis oriented parallel to the housing axis; a drive rod collar connected to the drive rod; a shuttle translatable along the drive rod and having a plurality of shuttle teeth; a pinion located proximate the shuttle and having a plurality of pinion teeth sized to mesh with the plurality of shuttle teeth; a first spring mechanically coupled to the first end of the housing, the first spring located coaxially with the drive rod; a first insert coupled to the shuttle and the first spring, the first insert defining a first insert shoulder arranged to contact the drive rod collar and drive the drive rod in a first linear direction under a first force generated by the first spring; a second spring mechanically coupled to the second end of the housing, the second spring located coaxially with the drive rod; and a second insert coupled to the shuttle and the second spring, the second insert defining a second insert shoulder arranged to contact the drive rod collar and drive the drive rod in a second linear direction under a second force generated by the second spring, wherein rotation of the pinion in a first rotational direction translates the shuttle in the second linear direction and rotation of the pinion in a second rotational direction translates the shuttle in the first linear direction, wherein when the shuttle is out of position to allow the plurality of shuttle teeth to mesh with the plurality of pinion teeth, the shuttle is movable by the first and second springs in the first and second directions.

In Example 17, the subject matter of Example 16 optionally includes wherein the pinion comprises: a pinion carriage; and a plurality of bearings that form the plurality of pinion teeth.

In Example 18, the subject matter of Example 17 optionally includes wherein the pinion carriage comprises a pinion plate defining a plurality of spokes, each of the plurality of bearings connected to a respective spoke of the pinion plate.

In Example 19, the subject matter of any one or more of Examples 17-18 optionally include wherein the pinion carriage comprises first and second pinion plates defining a plurality of spokes, each of the plurality of bearings located in between respective spokes of the first and second pinion plates.

In Example 20, the subject matter of any one or more of Examples 16-19 optionally include a motor; a switch; and a sensor arranged to detect a position of the shuttle and in electrical communication with the switch, wherein when the shuttle is out of position to allow the plurality of shuttle teeth to mesh with the plurality of pinion teeth, the switch severs electrical communication of the motor to a power supply.

In Example 21, the bi-spring surgical impact tools or systems of any one or any combination of Examples 1-20 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

As an alternative to a pneumatic piston driven system, disclosed herein are spring driven systems. Specifically, the surgical impact tools disclosed herein can include a bi-spring design. The surgical impact tools disclosed herein can include a housing that defines a cavity having a first end and a second end. A shuttle located within the cavity can define a plurality of indentations. As disclosed herein, a pinion located proximate the shuttle can have a plurality of protrusions sized to mesh with the plurality of indentations during rotation of the pinion. First and second springs can mechanically couple the housing to the shuttle. Rotation of the pinion in a first direction can translate the shuttle in a first direction towards the first end of the housing and rotation of the pinion in a second direction can translate the shuttle in a second direction towards the second end of the housing.

During use, when the protrusions and the indentations are no longer in a meshing engagement, the springs can cause the shuttle to move about a drive rod. The drive rod can be oriented along an axis of the housing and can extend from the first end of the housing to the second end of the housing. A drive rod collar can be affixed to the drive rod. An insert can be coupled to the first spring and arranged to impact the drive rod collar upon disengagement of the plurality of protrusions from the plurality of the indentations. The impact of the shuttle hitting the drive rod collar can cause the drive rod to transfer an impact force to a tool, such as a rasp, broach, etc., attached to a chuck of the surgical impact tool.

The pinion can include a pinion carriage and a plurality of bearings. The bearings can form the plurality of protrusions. The pinion carriage can include one or more pinion plates that define a plurality of spokes. Each of the plurality of bearings can be connected to a respective spoke of the pinion plate. When the pinion includes two pinion plates, each of the plurality of bearings can be located in between respective spokes of first and second pinion plates.

The surgical impact tool can include a motor that causes the pinion to rotate and move the shuttle. A switch can be electrically coupled to the motor and a sensor. The sensor can be arranged to detect a position of the shuttle. When the shuttle is out of position to allow the plurality of indentations of the shuttle to mesh with the plurality of the protrusions of the pinion, the switch can sever electrical communication of the motor to a power supply. The sensor can be a Hall effect sensor.

The above discussion is intended to provide an overview of subject matter of the present patent application. It is not intended to provide an exclusive or exhaustive explanation of the invention. The description below is included to provide further information about the present patent application.

Figure 1:
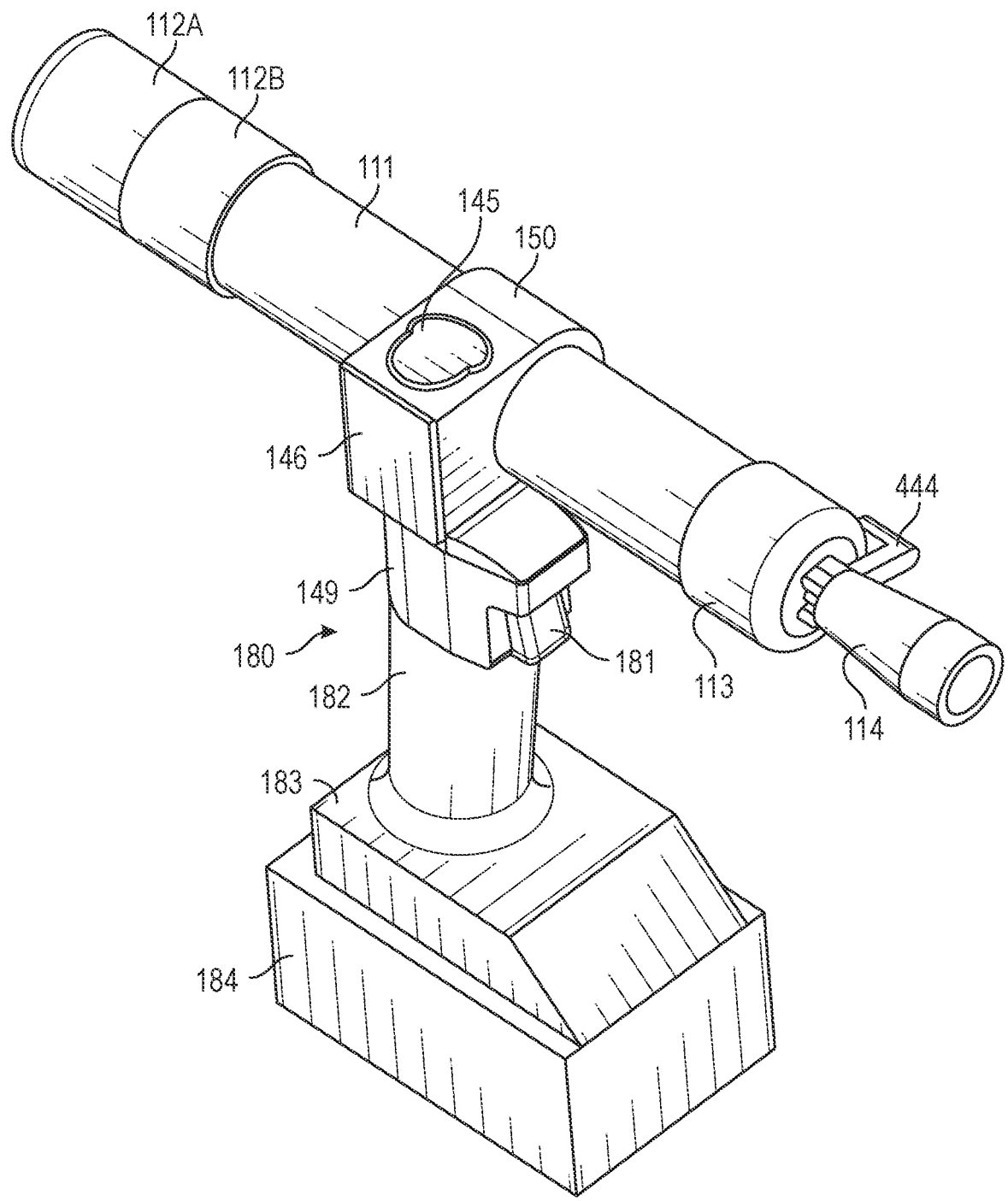
FIG. 1 shows an isometric view of bi-spring power impact tool consistent with at least one example of this disclosure.
Figure 2:
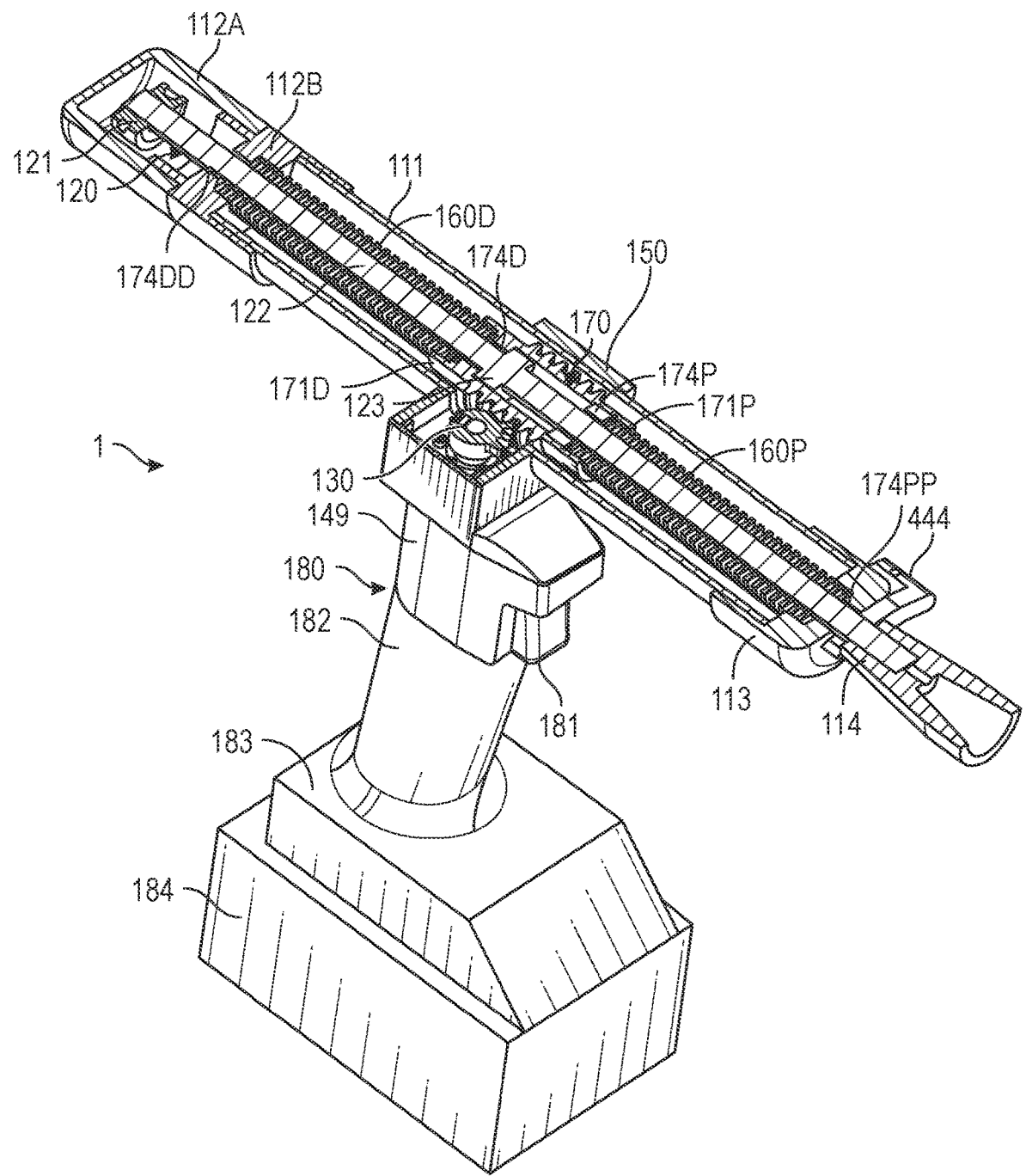
FIG. 2 shows an isometric cutaway view of a bi-spring power impact tool consistent with at least one example of this disclosure.
Figure 3:
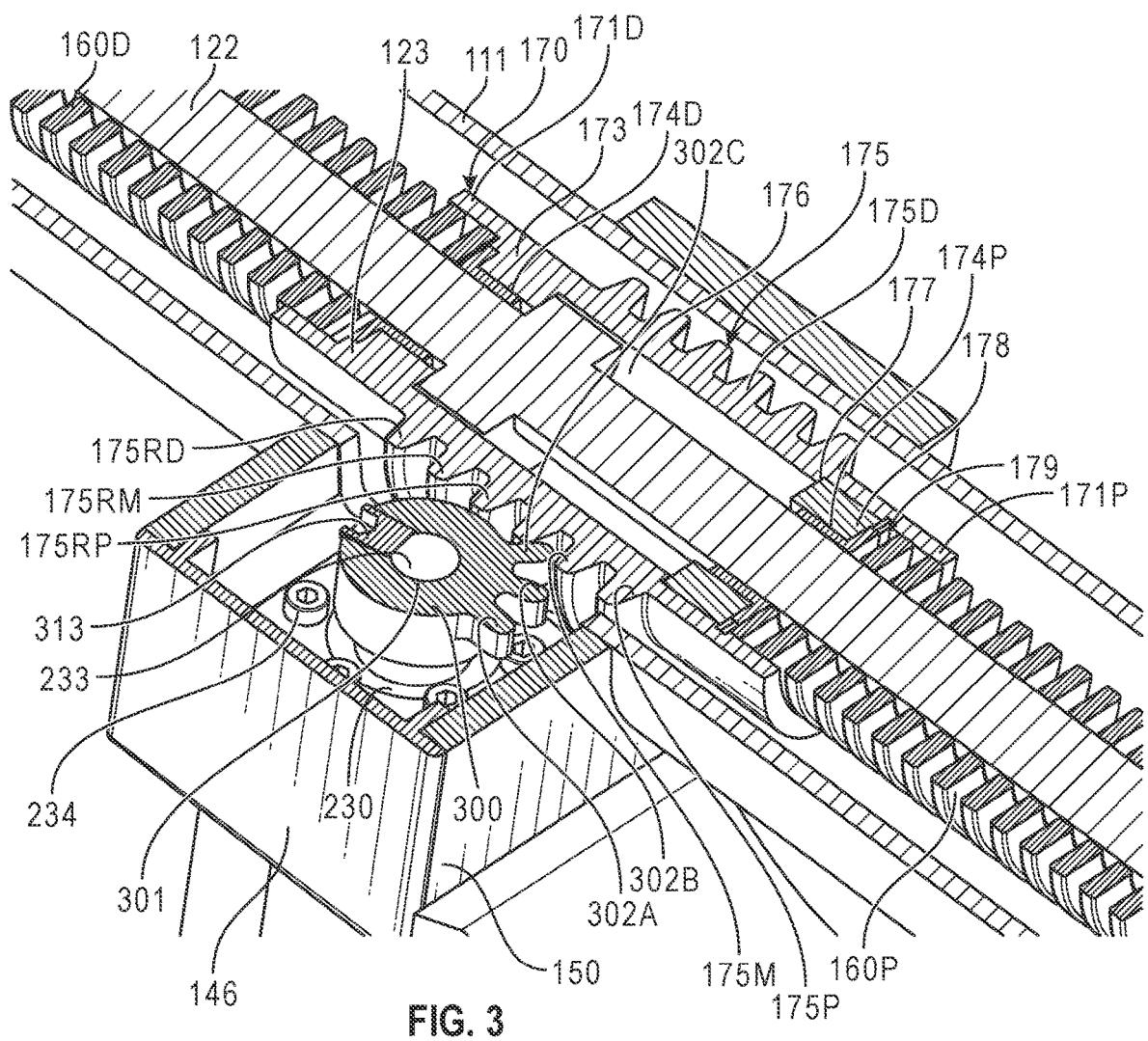
FIG. 3 shows a close-up isometric cutaway view of a bi-spring power impact tool consistent with at least one example of this disclosure.

Turning now to the figures, FIG. 1 shows an embodiment of a bi-spring power impact tool 1 according to various principles of the present disclosure. FIG. 2 shows an isometric cutaway view of the bi-spring power impact tool 1 in the neutral position, waiting to be activated. FIG. 3 shows a close up of the region around a motor mounting block (MMB) 150. The bi-spring power impact tool 1 can have a handle 180 with grip 182 and trigger 181 in an upper handle portion 149. A base 183 of the handle can contain a control circuit and can receive a removable and rechargeable battery 184, such as commonly used with cordless power tools. The top of the handle 180 can connect to the motor mounting block 150. The motor mounting block 150 can contain a mount for the gearmotor 230 (see FIGS. 9 and 10) and the spring and shuttle tube (SST) 110.

As shown in FIG. 2, the spring and shuttle tube 110 can include an outer tube 111 that contains a distal spring 160D and a proximal spring 160P, a shuttle 170 and a driver 120. The distal end of the spring and shuttle tube 110 can include an end cap 112B connected to a distal end of the outer tube 111, with a cover cap 112A connected to the end cap 112B. An end cap 113 can be provided at the proximal end of the outer tube 111. The end cap 113 can include an aperture with a proximal end of the driver 120 extending through the aperture. A tool holder 114 can be attached to the proximal end of the driver 120. The driver 120 can include an elongated drive rod 122. A stop collar 121 can be attached on the distal end of the rod 122. The stop collar 121 can be attached by a clamp-on, screw-on, clip-on or other connection method. An impact flange 123 can be disposed on a central region of the rod 122. The impact flange 123 can be formed integral with the rod 122 for structural integrity. The tool holder 114 can be attached to the proximal end of the drive rod 122 by threading, for example, so it can be easily changed if needed.

A soft blow clip (SBC) 444 can be snapped onto the drive rod 122. The soft blow clip 444 can alternatively slide onto the end cap 112B that could even allow for several different displacement settings by clicking into place to provide different settings for intensity of impact desired. A similar clip can be used at the distal end of the drive rod.

In another embodiment a rotary sleeve can be disposed between end cap 113 and tool holder 114 and can include an internal shelf disposed only on a portion of the rotary sleeve and the shelf can rotate to engage with a mating and similarly restricted shelf disposed on the proximal face of the end cap 113. Helical ramps adjacent to the shelves can allow the user to access the functionality of the soft blow clip 444 by rotation of the sleeve, providing similar displacement(s).

In the neutral state, the distal die spring 160D and proximal die spring 160P can be compressed (preloaded) to approximately half of their maximum deflection state (typically about 45% of their free length). The ends of the springs 160D and 160P can reside in counter bores 171D and 171P in the shuttle 170 respectively for the distal and proximal spring ends respectively that press on the shuttle 170 to maintain their coaxial alignment with the shuttle 170 and the drive rod 122.

The spring 160D, 160P can be die springs because the "coils" are made from rectangular cross section material so they tend to provide lateral rigidity to the spring so it is less likely to buckle sideways which could lead to rubbing (energy loss and especially when heavily compressed). Another design detail of efficient robust (low-wear) mechanisms is that helical (coil) springs can rotate slightly when they are compressed. Thus, when two springs are preloaded against the shuttle 170, one of the springs 160D, 160P can be made with a clockwise helix and the other of the springs 160D, 160P be made with a counterclockwise helix to counteract the rotation of one another and minimize rubbing induced energy losses and wear. Additionally, thrust washer can be used to allow for low friction rotation of the springs and shuttle mechanisms.

Referring to FIG. 3, the shuttle 170 can have integral annular gear rack drive teeth 175 (6 teeth are shown with a 16 pitch) which are offset with respect to the central plane of the shuttle 170 to enable proper fore and aft position for forward and reverse impact. A partial tooth pinion 300 can drivingly engage the shuttle 170. Three annular teeth 175 (the drive teeth 175P (proximal), 175M (middle) and 175D (distal)) of the shuttle 170 can be used for driving the shuttle 170 forward and three annular teeth (the retract teeth 175RP, 175RM and 175 RD) can be used for retracting the shuttle 170 forward. When the distal drive tooth 175D is offset from the center of shuttle 170 by a distance of P/2, the distal drive tooth 175D is positioned for initial engagement of the tooth 302C of the partial tooth pinion 300 at the start of the process for moving the shuttle 170 to displace the springs 160. However, because only a partial tooth pinion 300 is used, as tooth 302*a* comes around to re-engage the rack, an additional offset of about P/2 (plus about 1 mm for the 16 pitch gear as discussed below) is needed to ensure it does not collide with the drive tooth 175M (the middle drive tooth).

The springs 160D, 160P can be mounted on either side of the shuttle 170 with integral "annular" gear rack drive teeth 175 (the pitch diameter is infinite so the flanks of the teeth 175 need not be involutes but rather straight). The annular teeth 175 can wrap around the circumference of the shuttle 170 because when a coil spring is compressed, it can rotate slightly, and if a conventional section of a gear rack (straight across and not wrapped annular) were machined into the shuttle 170 (or mounted), as the shuttle 170 compresses the springs (e.g. 160P and 160D), its rotation can cause straight-across teeth 175 to rotate and edge load the drive gear 300 resulting in high contact stresses and early tooth wear. The shuttle 170 can include an inner cavity 176 that can be sized as shown in FIG. 3.

The shuttle 170 can be held concentric to the drive rod 122 with distal and proximal sliding contact flanged bearings 174D and 174P, respectively. Flanged bearings 174D and 174P can prevent rotation of the drive rod and therefore tool holder 114. Once installed and the springs are preloaded to the shuttle 170, the ends of springs 160D and 160P can keep the bearings 174D and 174P in place. The bearing can be manufactured from PEEK so as to allow for sliding contact and is steam sterilizable. Bearings 174DD and 174PP can center the drive rod 122 in the housing end caps 112*b* and 113, respectively. Bearings 174D and 174P can center the shuttle 170 on the drive rod 122 during cocking and can keep it centered while the shuttle 170 is moving fast to impact the driver 120's center impact flange 123.

As disclosed herein, the elements can be collinear, and this can result in the drive rod 122 being slender in order to fit down the center of the springs 160 and the shuttle 170. From a mass perspective, this can be beneficial because the mass of the drive rod 122, plus the mass of the tool holder 114 and the tool held therein can all be considered the system mass being driven by the impact force from the shuttle 170. However, as disclosed herein, the drive rod 122 can also support the shuttle 170 while it is being cocked, and if the gear tooth separation forces push radially too hard on the drive rod 122 for its size, it can deflect and cause the gear teeth to skip.

In the neutral state, such as just after the driver 120's impact flange 123 has been impacted on its distal side by shuttle 170's distal flange 173, the springs 160 can have oscillated for a few cycles after impact but have come to rest, typically is 5-10 cycles which will take a on the order of 100-200 milliseconds as the natural frequency of the shuttle 170 can be about 40 Hz. The impact can be a mix of elastic and inelastic and while one might think that a heavier shuttle 170 may be better for energy transfer, too heavy and the speed will be slow including the time to come to rest because the natural frequency will be low. The blows per second required by the surgeon, typically in the range of 1-10, can be selected by the surgeon and controlled by the control circuits in the base 183), which are governed by the rotation of the partial tooth pinion (PTP) 300 by the gearmotor 230. The gearmotor 230 can revolve at a constant rate during the period of use for a set rate of impacts as this allows the gearmotor 230's reflected rotational inertia at the PTP 300, which is considerable, to contribute to the effort to cock the shuttle 170 for another strike, thereby helping with overall system efficiency and increased battery life.

To rotate at a constant speed for a set impact rate, once the last tooth 302A has cleared the shuttle proximal drive tooth 175P, the shuttle 170 can be propelled forward by the stored energy in the springs 160D and 160P. As disclosed herein, the two opposed compression springs each of stiffness k can both contribute to the forward energy of the system, because they are preloaded against each other. They act as one with bidirectional stiffness 2k as long as they are preloaded against each other. Meanwhile, as the shuttle 170 is accelerating forward increasing its kinetic energy as it is transferred to the shuttle 170 from the stored potential energy in the springs 160D and 160P, the PTP 300 continues to rotate. The shuttle 170 impacts the drive rod 120 and settles down in time for PTP tooth 302C to have come around and make contact with the shuttle distal drive tooth 175D as shown in the system neutral position in FIGS. 2 and 3.

Figure 4:
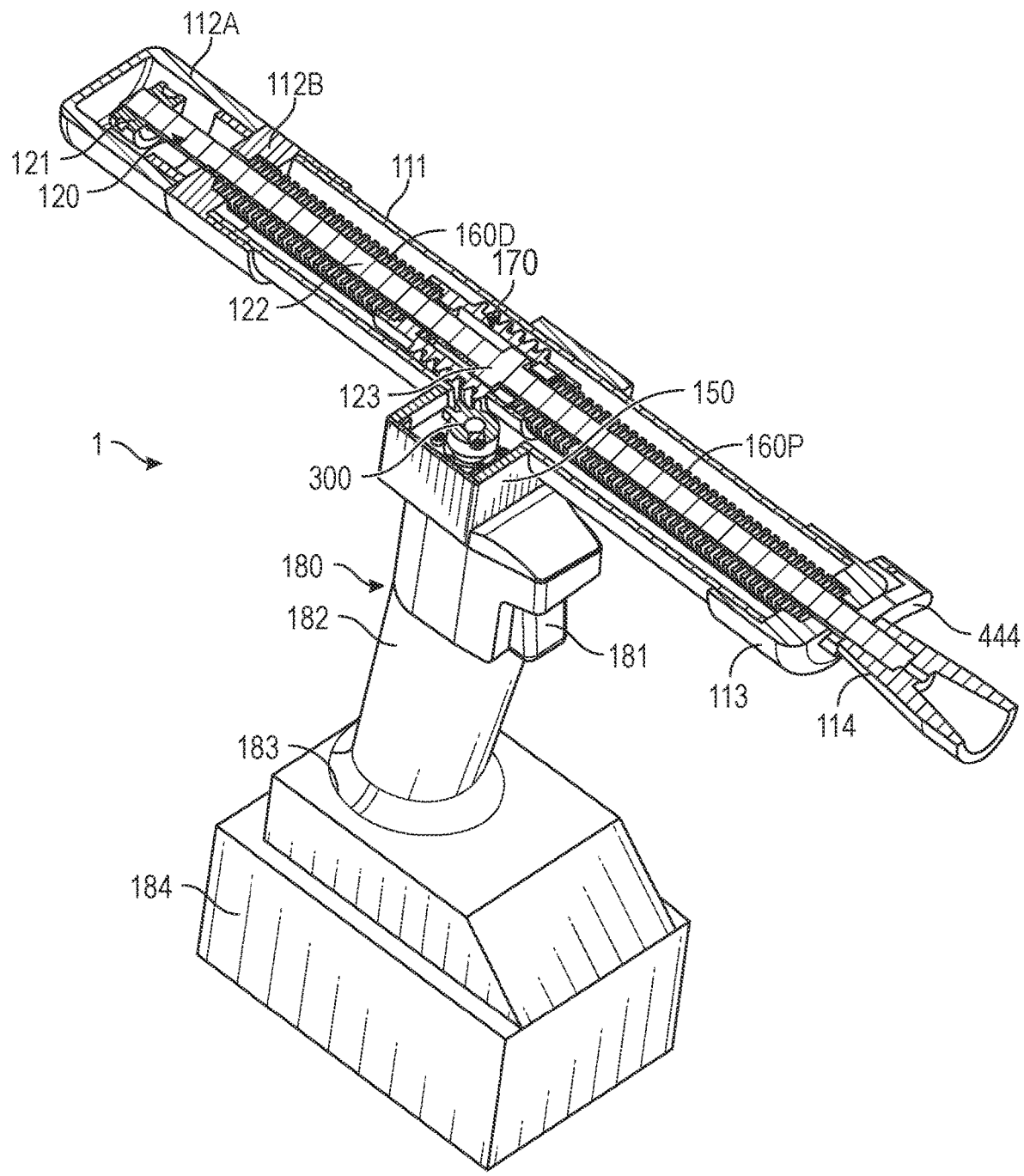
FIG. 4 shows an isometric cutaway view of a bi-spring power impact tool consistent with at least one example of this disclosure.
Figure 5:
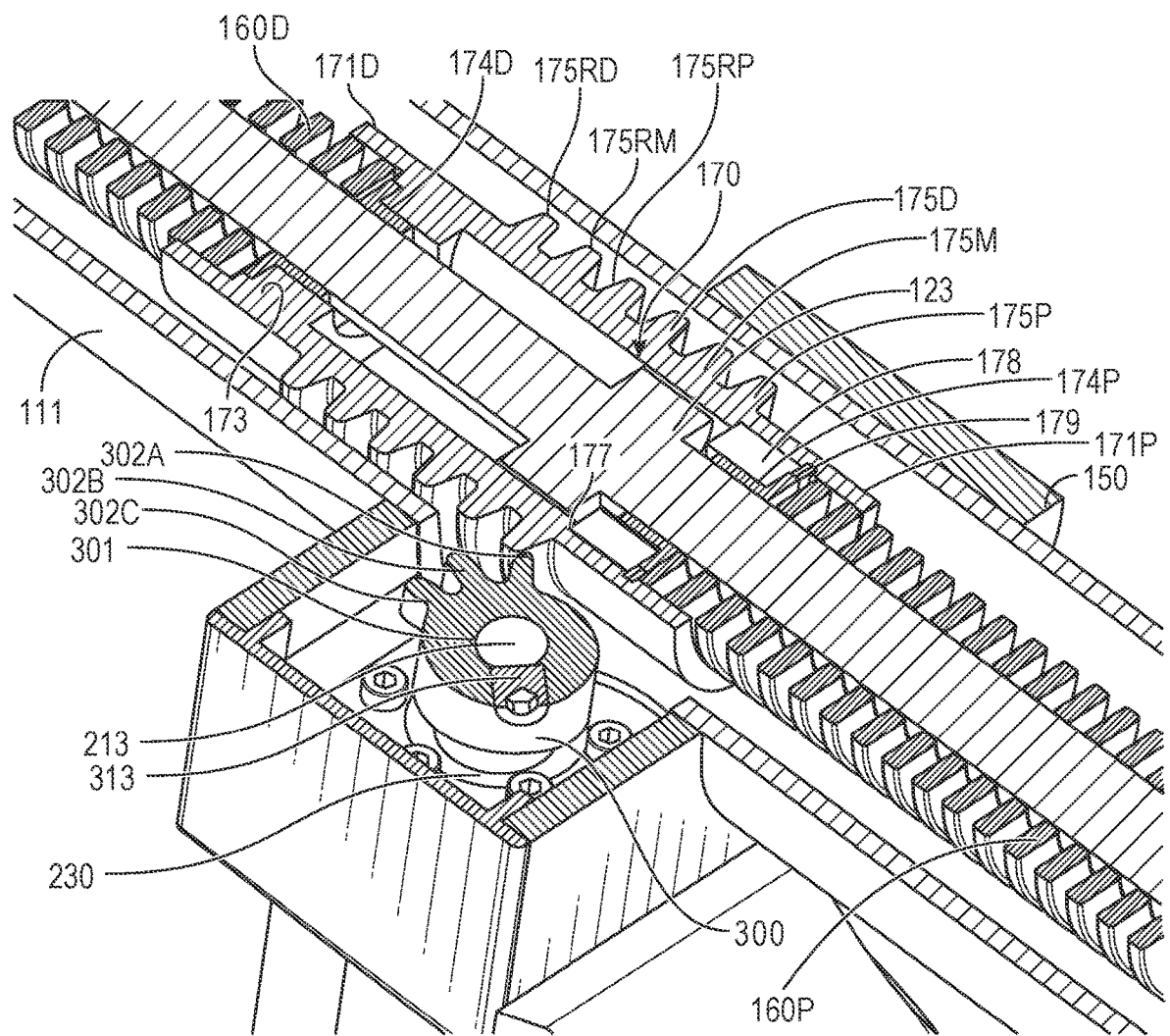
FIG. 5 shows a close-up isometric cutaway view of a bi-spring power impact tool consistent with at least one example of this disclosure.
Figure 16A:
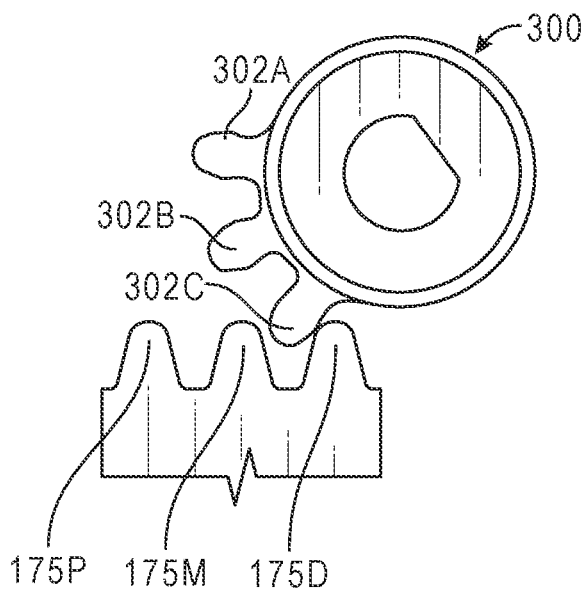
FIGS. 16A, 16B, and 16C each illustrates different stages of engagement of a partial tooth pinion and the shuttle's gear teeth consistent with at least one example of this disclosure.
Figure 16B:
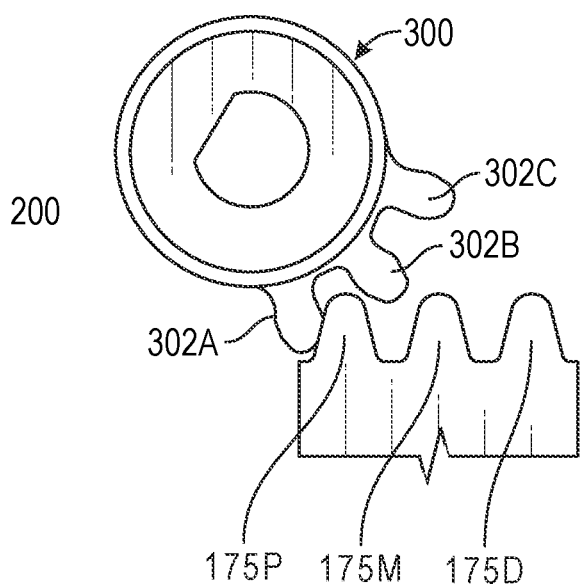
Figure 16C:
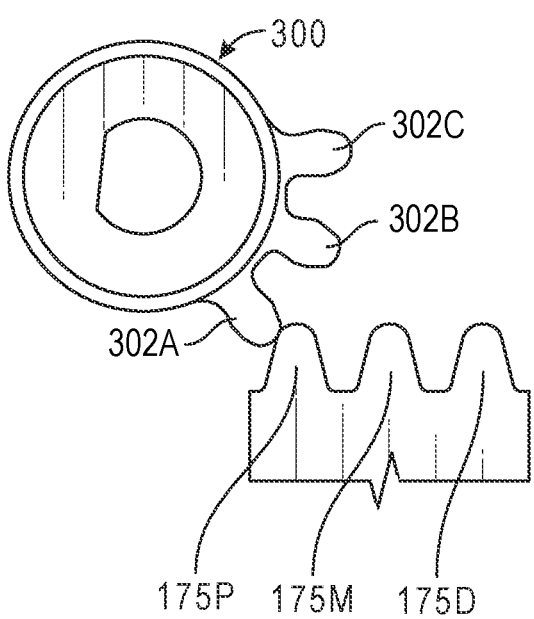

For full strength forward impact, the user can push the bi-spring powered impact tool 1 forward such that the soft blow clip (SBC) 444 (or another spacer embodiment) can be pressed against the proximal surface of the end cap 113, which can displace the drive rod 120's impact flange 123 backwards. The impact flange 123's distal face can then be pressed against the proximal face of the shuttle 170's impact flange 173. At this point the PTP tooth 302C can have engaged the shuttle distal drive tooth 175D and turned counterclockwise as shown will move the shuttle 170 back to the ready-to-fire position shown in FIGS. 4 and 5. FIG. 16 shows the progression of steps from initial making of tooth contact (a), to the end of rolling contact between the involute teeth (b), to the final displaced position where the tooth 302A breaks contact with the shuttle proximal drive tooth 175P.

Rotation of the PTP 300 from initial contact to final moment of rolling can cause linear motion of the rack as shown in FIG. 16. The tooth 302A can break contact with the shuttle drive tooth 175P and the shuttle 170 is thus released and accelerates towards the driver 120's impact flange 123. During this period of motion, there can be sliding contact between tooth 302A and 175P. If finer resolution of motion is desired, a finer pitch can be used but then the teeth may be smaller and weaker.

The gear teeth base material (e.g., 175 and 302) can be hardened (RC50 or more), ground with tips rounded and coated with a wear resistant coating, such as tungsten carbide applied by physical vapor deposition. As the teeth are not large with respect to depth of contact stresses, they can be through hardened. A dry laminar solid lubricant can also be applied during the coating process, one such as tungsten disulfide $WS_2$, a soft lamellar material similar to graphite/$MoS_2$. Also note that since the coating has a much higher modulus of elasticity and strength than the base steel of the gear the contact stress can be limited by that of the steel, for if the steel should yield below the coating layer thickness, the coating would peel off. In a gear with full circumference of teeth engaging another gear with full circumference of teeth, the tooth tip edge does not make high stress contact and thus is generally not rounded over; yet here the last tooth's tip does make high force contact with the rack teeth just before firing. This tooth tip edge to edge contact is like the edges of a trigger system, and thus care can be needed to prevent unacceptable wear.

Driver 120's impact flange 123 can be impacted on its distal face to produce force in the forward (proximal) direction for driving a tool into an object (e.g., a femur) by distal drive flange 173's proximal face. The distal drive flange 173 can be integrally made with the shuttle 170 as it can be subject to the highest stresses. The distal spring 160D can be coaxial with the driver 120 and the flange 123 and thus force can be applied directly to the opposite side of the flange that impacts the driver flange 123 thereby making a very robust design.

Figure 6:
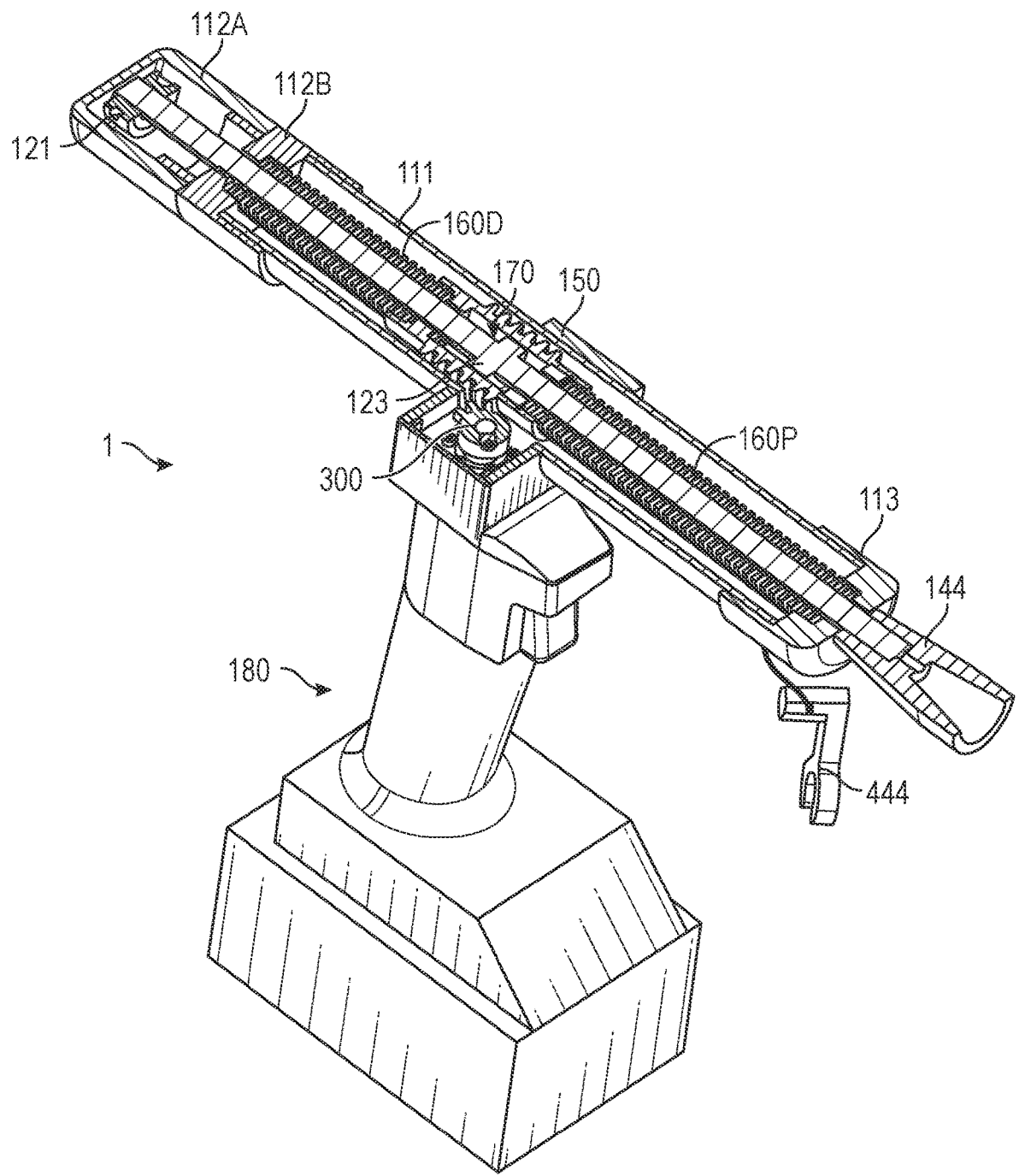
FIG. 6 shows an isometric cutaway view of a bi-spring power impact tool consistent with at least one example of this disclosure.
Figure 7:
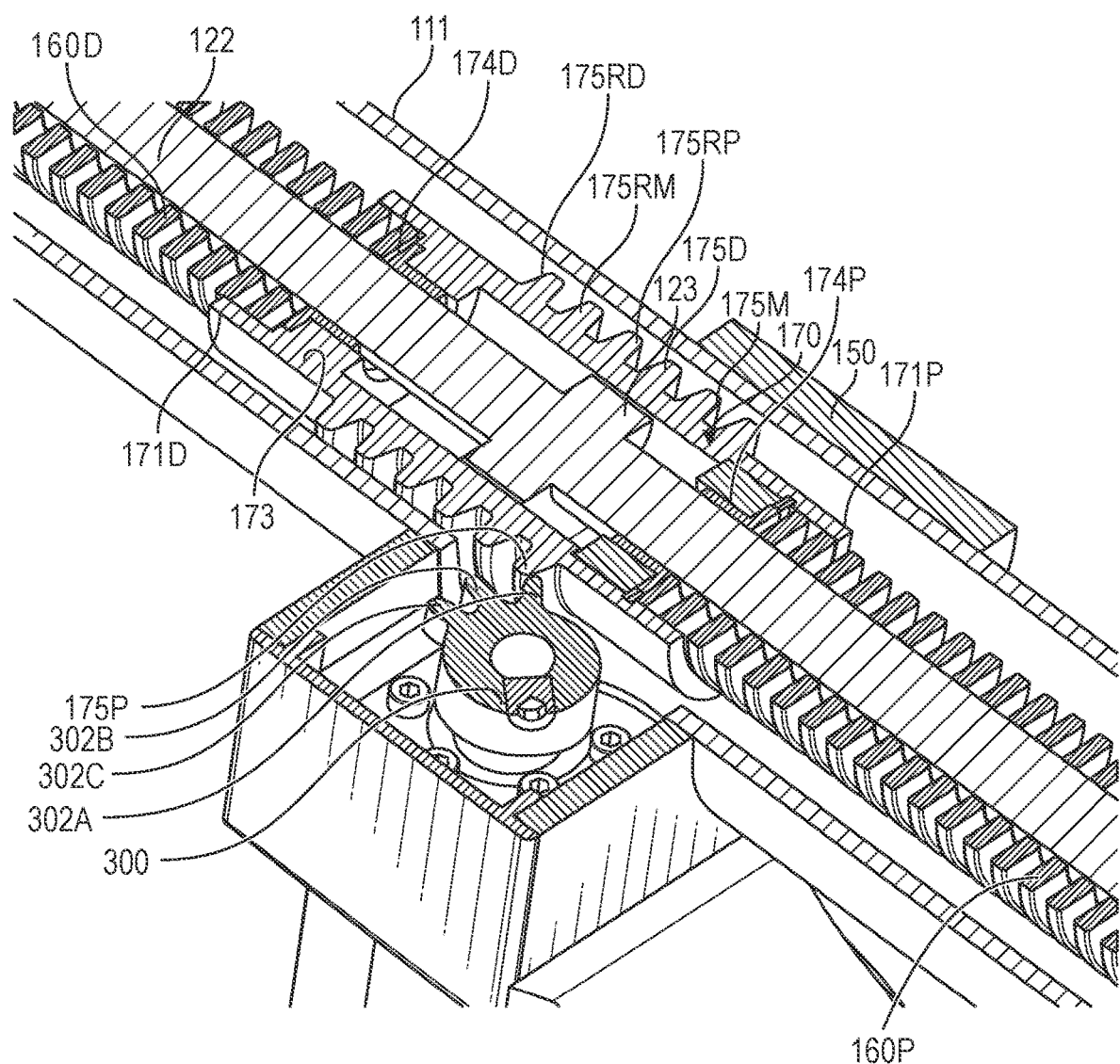
FIG. 7 shows a close-up isometric cutaway view of a bi-spring power impact tool consistent with at least one example of this disclosure.
Figure 12:
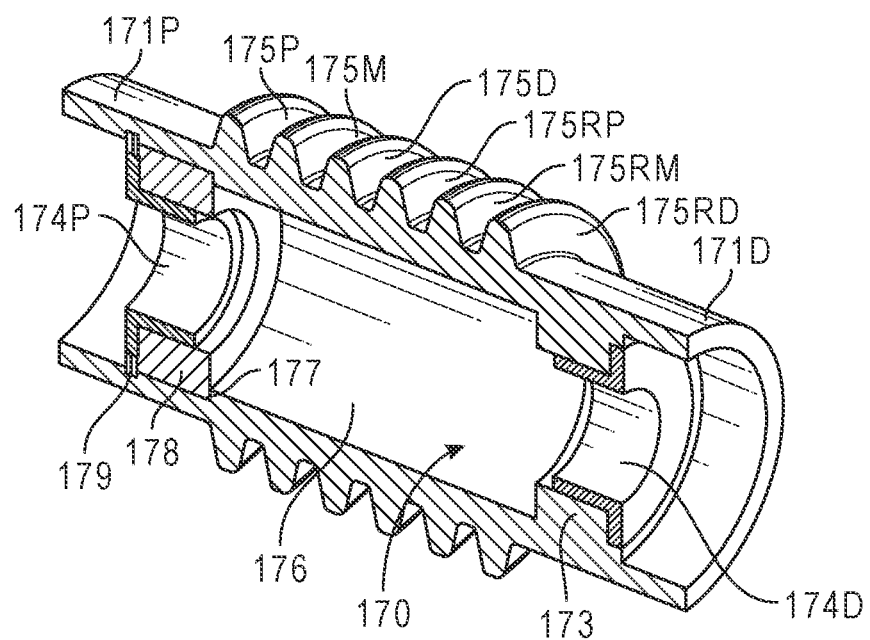
FIG. 12 shows a cross-sectional isometric view of a shuttle consistent with at least one example of this disclosure.
Figure 13:
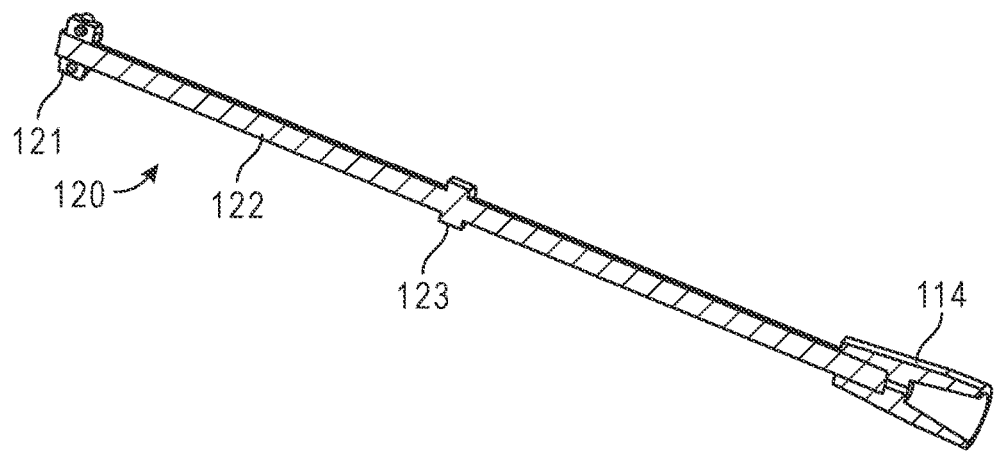
FIG. 13 shows a cross-sectional isometric view of a drive rod subassembly consistent with at least one example of this disclosure.
Figure 14:
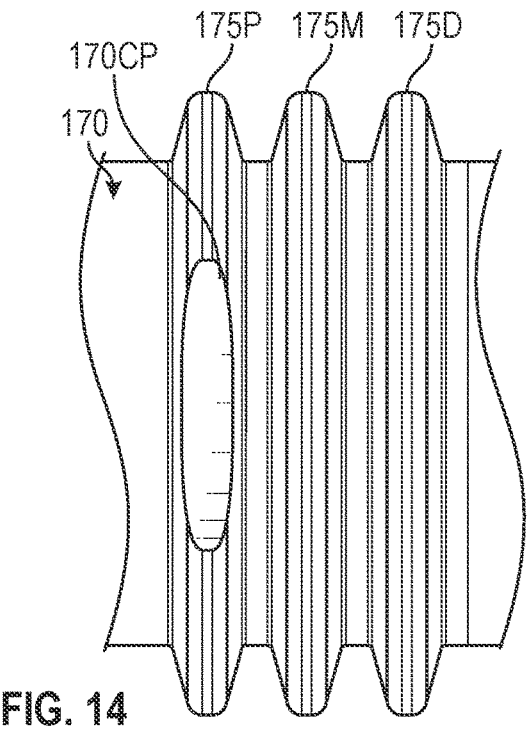
FIG. 14 shows the contact radius of a shuttle member's circular gear rack consistent with at least one example of this disclosure.
Figure 15:
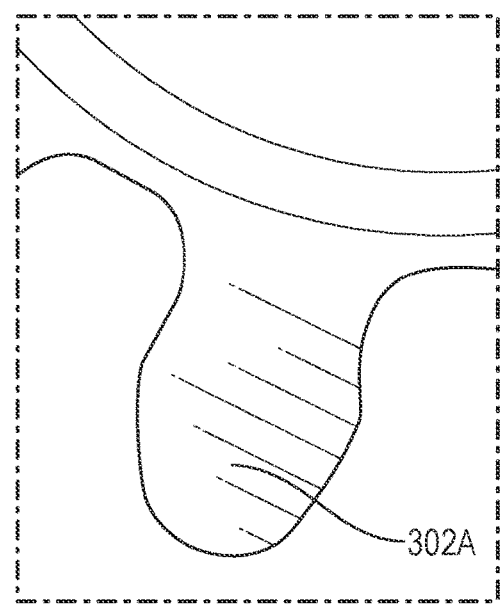
FIG. 15 shows the contact radius of a drive gear's tooth consistent with at least one example of this disclosure.

For retraction of the driver 120, as shown in FIGS. 6 and 7 (and see FIGS. 2 and 12 for the shuttle's 170 components), the flange insert 178, which can be seated against counterbore face 177 in the shuttle 170's proximal end, can be held in place with internal snap ring 179. In the retract mode the force does not have to be as high. This can be adjusted at assembly by making the driver 120's end clamp on stop collar 121 (see FIG. 13). A snap ring can take the load, but it may be somewhat more dissipative (i.e., less efficient) than the integral flange 173.

Figure 8:
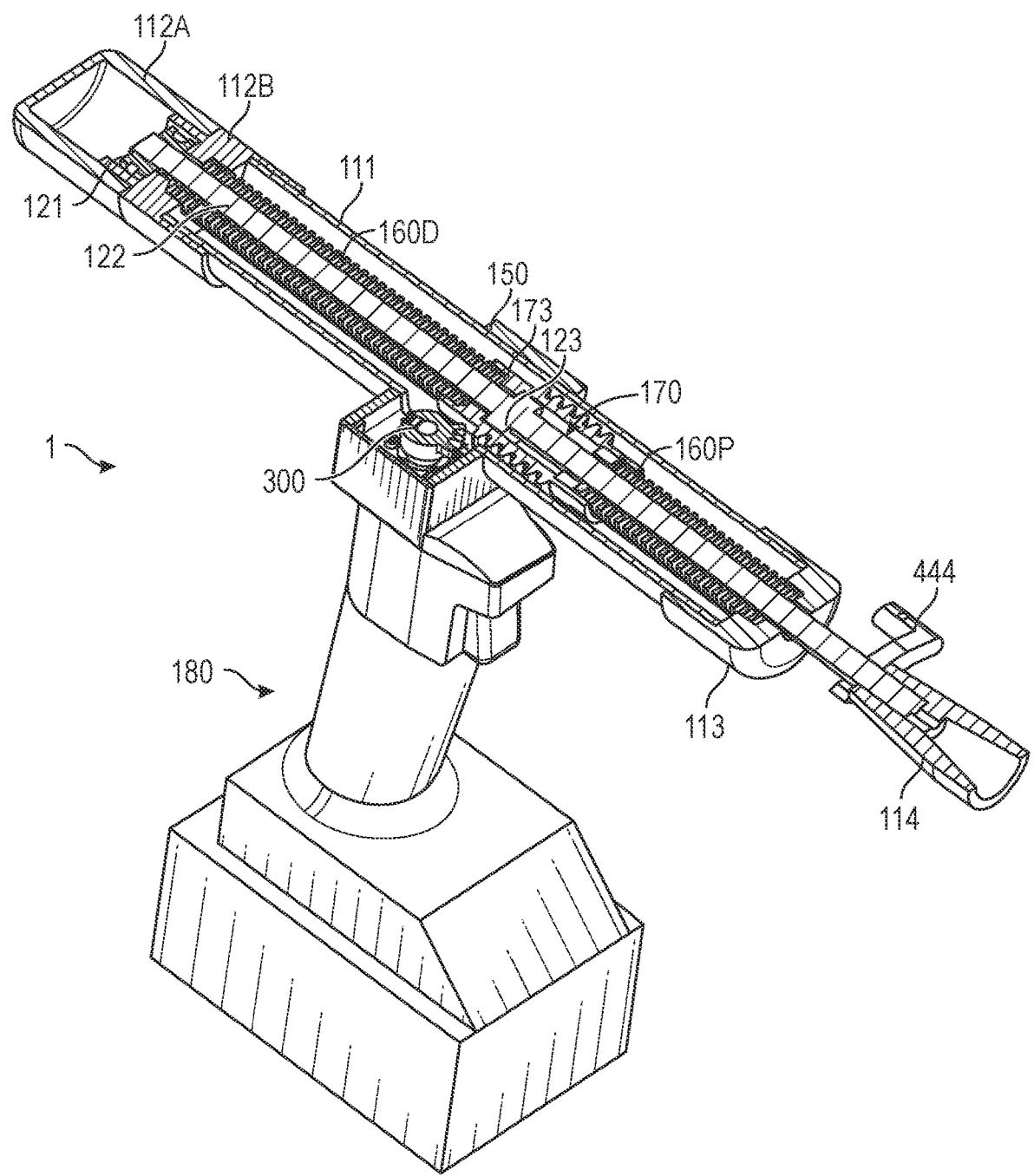
FIG. 8 shows an isometric cutaway view of a bi-spring power impact tool consistent with at least one example of this disclosure.

For rearward impact to extract a tool, the user can pull the bi-spring impact tool 1 backwards such that stop end collar 121 is pressed against the counterbore in end cap 112B and the proximal surface of the driver 120's impact flange 123 faces the distal surface of the shuttle's flange insert 178. Selecting reverse (e.g., by a reverse button on the handle 180) and activating the gearmotor 230 (e.g., with the switch 181 on the handle 180), the PTP 300 can rotate in the opposite direction for forward impact, and now the PTP tooth 302A can engage the shuttle 170's proximal retract tooth 175RP and turning clockwise as shown, can move the shuttle 170 forward to the ready-to-fire position, shown in FIG. 8, until the tooth 302C breaks contact with the shuttle 170's distal retract tooth 175RD at which point the springs 160 move the shuttle 170 rearward at high speed until the driver's impact flange 123 proximal surface is impacted by the distal surface of the shuttle's flange insert 178. The shuttle 170 can have three teeth for retraction, 175RP, 175RM, and 175RD (i.e., proximal, middle, distal retract teeth respectively), each in this embodiment that can be engaged by the three teeth on the PTP 300.

Figure 11:
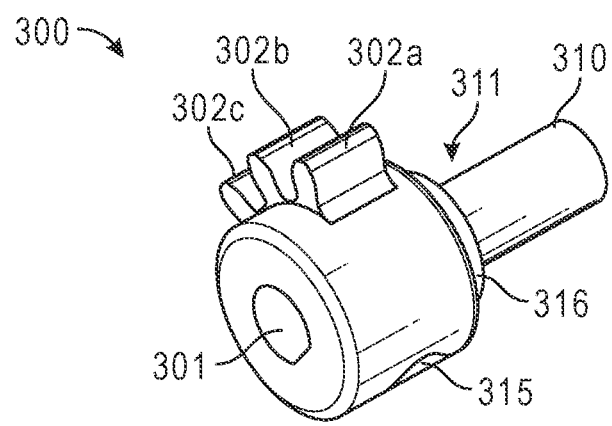
FIG. 11 shows an isometric view of a partial tooth pinion (drive gear) consistent with at least one example of this disclosure.

The shuttle 170's circular gear rack drive teeth 175 can be driven by the teeth 302 on the partial tooth pinion 300 (see FIG. 11) which can have a D-shape bore 301 to slidingly fit onto the gear motor's D-shaped output shaft 233. In FIG. 3 the front flange of the gearmotor 230 can be seen, but one of the bolts 234 that hold it in place is hidden behind partial tooth pinion 300. A fastener, such as a flat tip setscrew 313, can hold partial tooth pinion 300 in place although as will be discussed, the PTP 300 is axially constrained but the gearmotor shaft and outrigger support bearings (see FIG. 9). For the illustrated embodiment, three teeth, 302A, 302B, and 302C as determined by the gear pitch and pitch diameter are needed to drive the rack the desired distance in either direction.

The rear collar 121 on the rod 122 is shown as a fixed clamp collar, but to adjust the retraction force, it could easily be a threaded collar on the shaft so the surgeon can rotate the collar and adjust its axial position with respect to the flange 123. In this case, the rear cap 112A could be removable or the threaded collar have a protrusion through it for dialing the position.

In forward and reverse impacts, the energy can be changed by changing the distance the shuttle travels (accelerates) before it impacts the flange 123. Thus, the spring stiffness (spring size) can be fixed to the maximum of what may ever be needed, and with great sensitivity the energy achieved per blow is easily adjusted by changing the position of the flange 123 inside the shuttle cavity 176. This can enable great robustness of design, as it is not a slip clutch or other energy robbing element.

Motor gearbox combinations ("gearmotor'"), particularly those with high ratios, can output very high torques. Often this torque can be transmitted to another shaft with a coupling. Sometimes a gear or pulley can be directly attached to the gearmotor output shaft. However, in this case, especially since there may be a shock load of the load on the drive gear (PTP 300) suddenly being released, it may be found that the equivalent radial load of the torque transmitted divided by the pitch radius of the gear exceeds the allowable radial load on the gearmotor 230 output shaft 233. It can be possible to position the gear teeth (e.g., teeth 302) tight against the face of the motor with the gear hub on the outside, here this is not shown because the shuttle 170's circular rack teeth 175 would contact the face of gearmotor 230.

Figure 9:
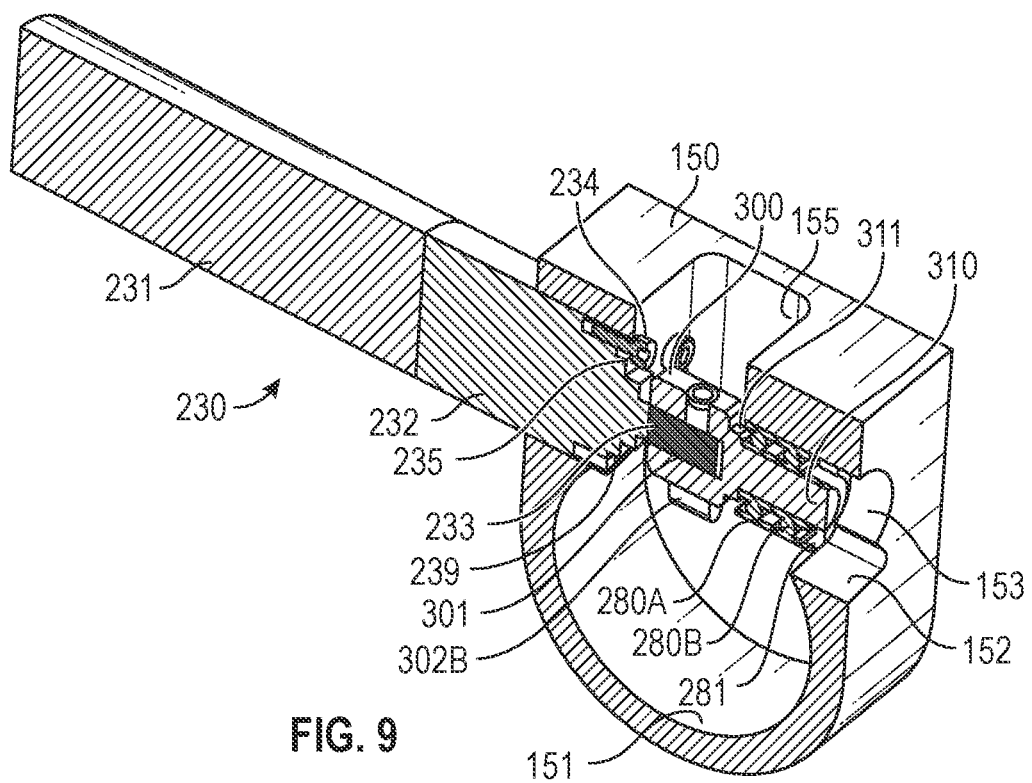
FIG. 9 shows a cutaway isometric view of a gear motor housing subassembly consistent with at least one example of this disclosure.
Figure 10:
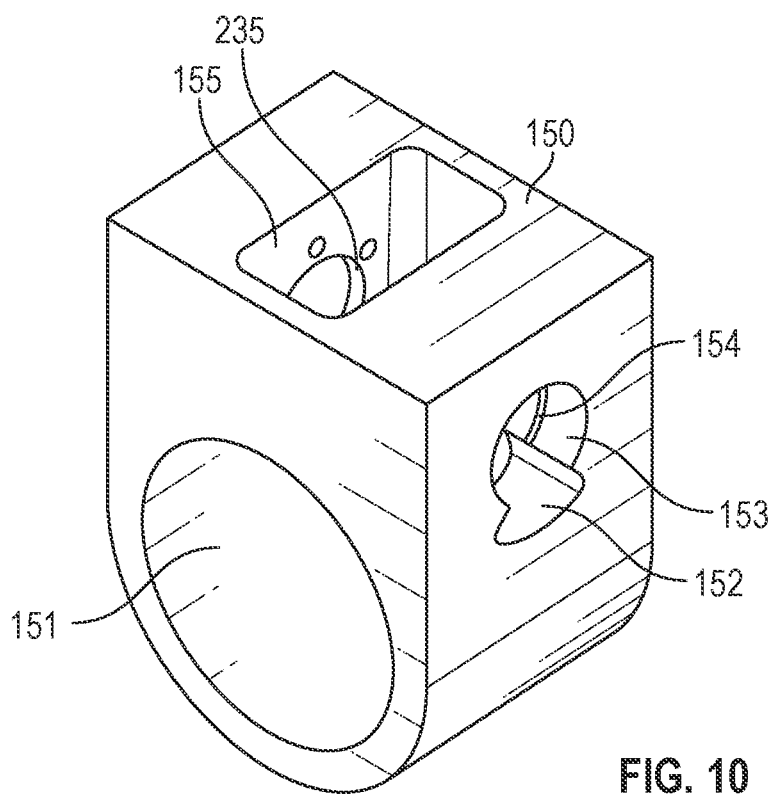
FIG. 10 shows a cutaway isometric view of a gear motor housing consistent with at least one example of this disclosure.

As shown in FIGS. 9 and 10, a gearmotor's front faces can have a precision round locating boss which can be concentric with their inner bearings that supports the output shaft 233. Hence, they can be mounted such that the boss can be a sliding fit in a precision bore 153, which can extend across the region in which the shuttle 170 passes to the other side of the MMB 150 where precision outrigger support bearing(s) 280 can be placed. The bore diameter for the locating boss can be the same as the bore 153 required for the outrigger bearing 280, so a straight through line bore operation can be made and the hole reamed to exact tolerances.

In the center region of the structure into which the precision bore 153 has been made, a cavity can be made which contains the partial tooth pinion (PTP) 300 on an integrally formed gear shaft structure 311. On this gear shaft structure 311, on the gear end (PTP 300), the diameter can be big enough for a precision bore to mate with the gearmotor shaft 233, including a shaft feature such as a flat, keyway or spline so excellent torque transmission can be obtained without the need for a coupling. The other end of shaft structure 311 can have a shaft 310 that fits into the outrigger bearing(s) 280. Two bearings 280 can be used to give some additional moment support and stiffness. The effect can be a simply supported shaft (structure 311) with a gear (PTP 300) essentially in the middle and the radial load from the gear teeth (302B) tangential force, as well as gear tooth separation forces, is shared by the gearmotor shaft support bearings and the outrigger bearings 280. However, the precision fits and alignment obtained by this arrangement can be made possible by the monolithic structure of the motor mounting block.

As shown in FIGS. 9 and 10, since the gear tooth tangential and separation forces always essentially add to have a net upwards direction, the outrigger bearings' bore 153 can have its lower quadrant relieved to form a fan-shaped access 152 enabling the partial tooth gear 300 to be slid into place. A snap ring groove 154 in the bore 153 can hold a snap ring 281 that can axially retain the bearings in the bore 153, which can be covered in the fully assembled device by the cap 145 (see FIG. 1). A top access port 155 can allow access to tighten bolts 234 to hold the gearmotor 230's gearhead 232 securely to the housing 149. This access port can be covered in the fully assembled device by the cap 146 (see FIG. 1). The bore 235 can be collinear and the same diameter as bore 153 so they can be line-bored for high precision. The gearmotor front boss 239 can be precisely held concentric as discussed above. By selecting outrigger bearings 280A and 280B to have the same outside diameter as the boss 239, the PTP shaft 310 can fit in the bearings' 280 bores, and the PTP D-shape bore 301 can slide over the gearmotor shaft 233, the bearings in the gearmotor 230 will not be over constrained by the outrigger bearings 280A and 280B, which can seat against shaft 310's shoulder 316. As a result, high radial loads due to tangential and gear tooth separation forces on the gear teeth 302, can be shared by the bearings in the gearmotor 230 and the outrigger bearings 280.

In the case of the circular gear rack teeth 175 shown herein, the crown of the gear rack tooth can operate to hinder misalignment. Note that this crowning can result in higher contact stresses than a conventional flat flank gear rack tooth engaging with a drive gear would experience, but this can be engineered as shown here with advanced analysis of the system that includes not only calculation of the gear tooth strength but also of the contact stress of the drive gear teeth 302 with the circular gear rack teeth 175.

The rear face of the tool holder 114, which can be attached to the end of drive rod 122, can come into contact with the front of the system's outer tube 111 front end cap 113. The center impact flange 123 of the drive rod 120 can be positioned within the system such that as when the shuttle 170 is cocked, its proximal flange (nearest the tool holder 114) inner face is just in contact, or a tolerance clearance of about one mm to prevent an over constraint condition where the drive gear 300 has just a little bit more to go before it can release and fire the shuttle 170, but the drive rod 122 impact flange 123 is already in contact with the shuttle 170's proximal flange inner surface (see FIGS. 2 and 3).

Figure 17:
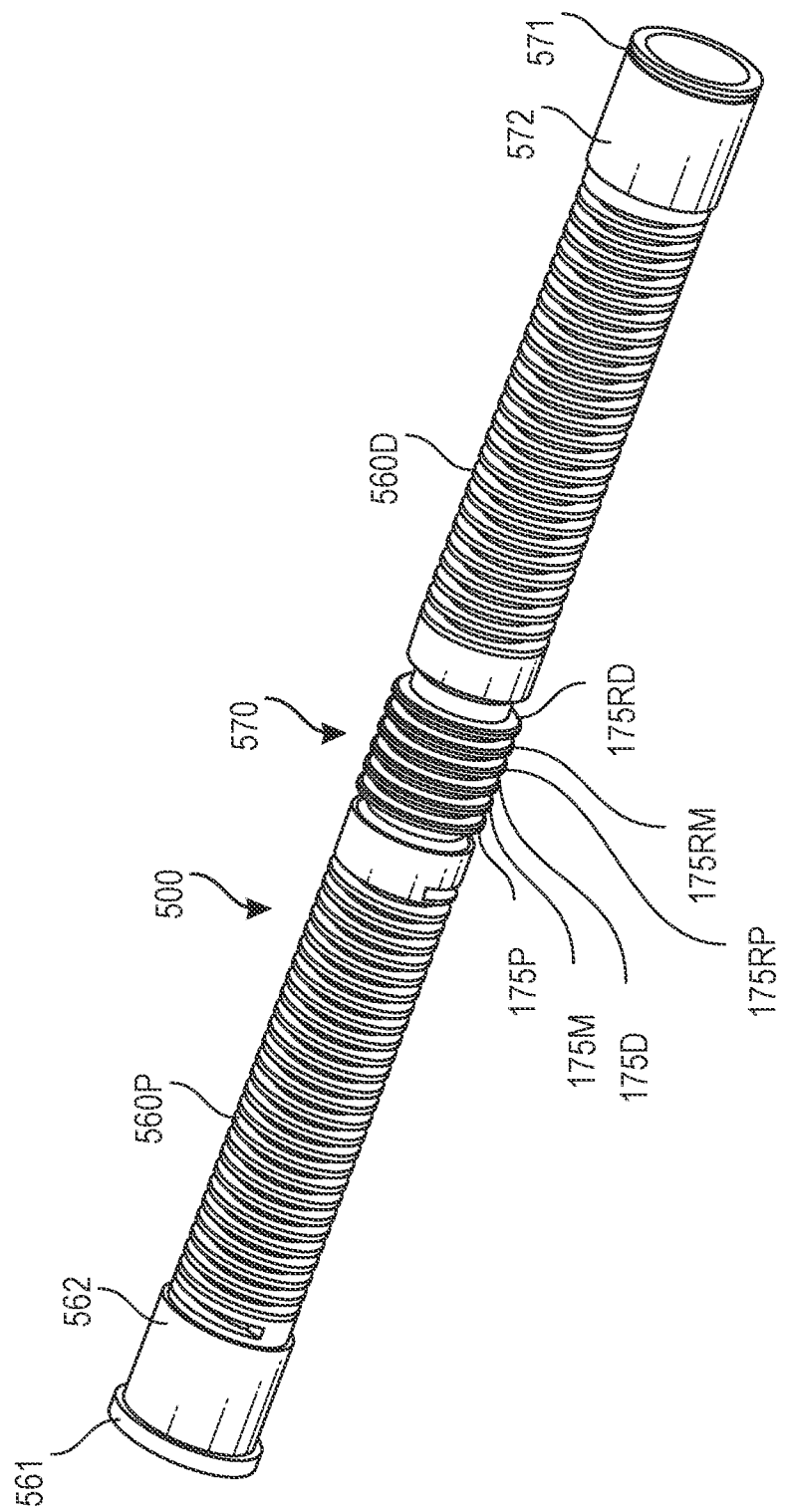
FIG. 17 is an isometric view of a monolithic machined spring and shuttle consistent with at least one example of this disclosure.

In a second embodiment shown in FIG. 17, a monolithic spring shuttle structure (SSS) 500 can include the two springs 560P and 560D and the shuttle section 570 with integral gear teeth. The springs can be machined with 560P being CW and 560D being CCW. It can be made integral by machining the springs from a steel rod or tube. The circular rack teeth 175 can still be machined into shuttle section 570. The forward impact surface for driving the tool forward can be monolithic with the shuttle 500, but if desired a high force capacity snap ring could be used. Using a custom machined spring, the advantage is a larger diameter somewhat shorter spring can be used which also incorporates the end caps needed to mate with the spring and shuttle tube (SST) 110. In this case, one spring 560 is clockwise and one is machined counterclockwise, so there is no net appreciable torque on the ends that attach to the outer tube 111, thus sliding or wear are avoided. Preload can be obtained when the system's outer tube 111 would be placed over SSS 500 and then the proximal end of the tube seats against flange 561. SSS 500 would be gripped from the inside (e.g., with an expansion tool) and pulled in tension until a snap ring would be fitted into groove 571. The SSS 500 can be kept centered in the outer housing tube 111 by end bosses 562 and 572 that would be typically about 2-3 mm larger in diameter than the outside diameter of the circular rack gears 175P, 175M, 175D and 175RP, 175RM and 175RD for forward (drive) and rearward (retract) impact actuation of the shuttle section 570.

Figure 18A:
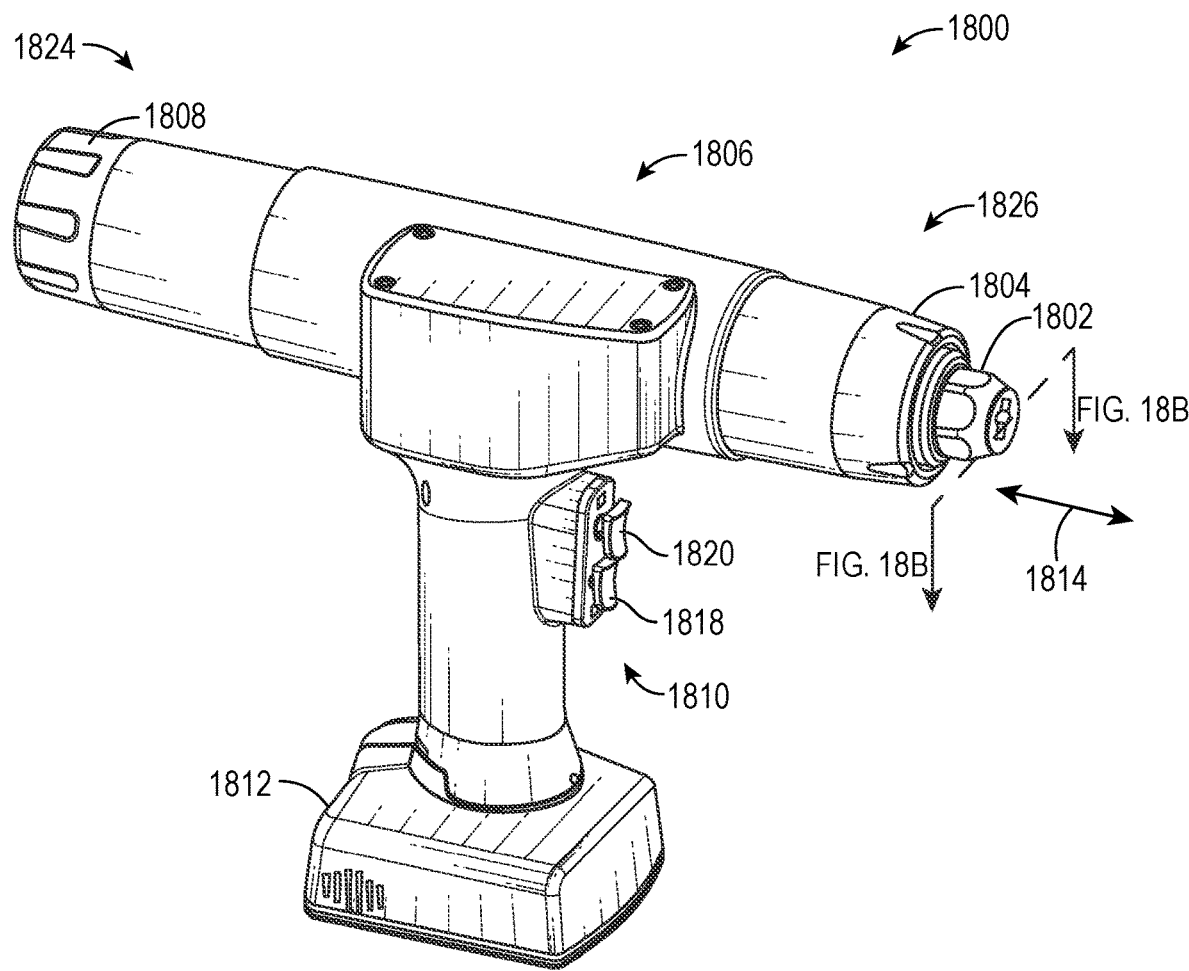
FIG. 18A shows a bi-spring surgical impact tool consistent with at least one example of this disclosure.
Figure 18B:
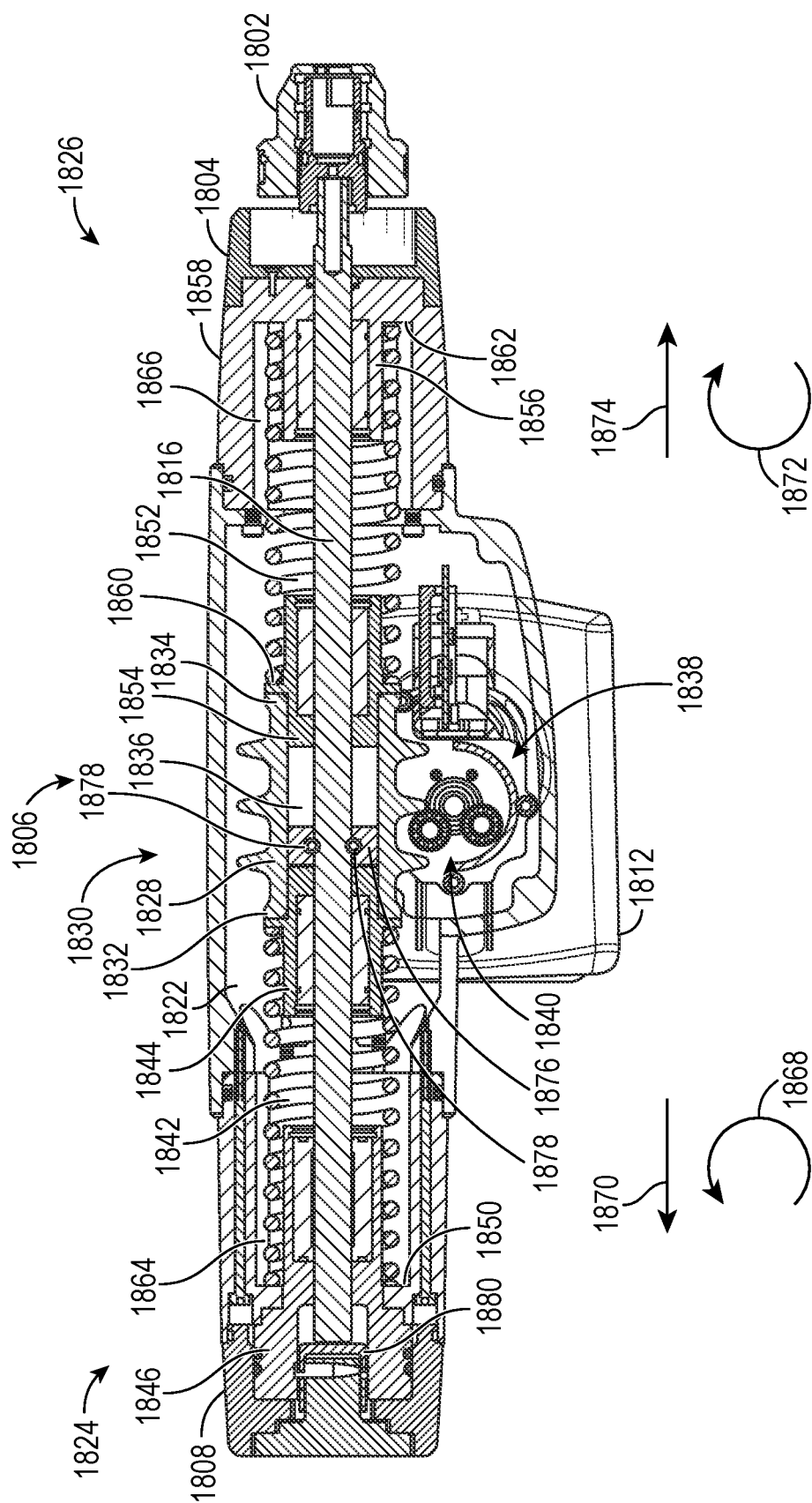
FIG. 18B shows a section view of the bi-spring surgical impact tool of FIG. 18A consistent with at least one example of this disclosure.

FIG. 18A shows a bi-spring surgical impact tool 1800 consistent with at least one example of this disclosure. FIG. 18B shows a section view of the bi-spring surgical impact tool 1800 consistent with at least one example of this disclosure. The impact tool 1800 can include a chuck 1802, a chuck shroud 1804, a housing 1806, an end cap 1808, a trigger group 1810, and a battery 1812. The chuck shroud 1804 can allow the chuck 1802 to move as indicated by arrow 1814 without exposing a drive rod 1816 as disclosed herein. During use, a surgeon may press a first trigger 1818 to drive a tool or a second trigger 1820 to extract a tool as disclosed herein. For example, to drive a broach the surgeon may press the first trigger 1818 and to remove the broach from a bone the surgeon may press the second trigger 1820.

Housing 1806 can define a cavity 1822 a first end 1824 and a second end 1826. A shuttle 1828 can be located within the cavity 1822 and define a plurality of indentations 1830, sometimes called shuttle teeth. The shuttle 1828 can have a first end 1832 and a second end 1834. The shuttle 1828 can define a through hole 1836. The drive rod 1816 can pass through the through hole 1836 and the shuttle 1828 can translate in a first direction and a second direction along the drive rod 1816 as disclosed herein to generate impact and extraction forces. For example, a pinion 1838 can be located proximate shuttle 1828 and have a plurality of protrusions 1840, sometimes referred to as pinion teeth, sized to mesh with indentations 1830 during rotation of the pinion 1838 as disclosed herein.

A first spring 1842 can mechanically couple the first end 1824 of the housing 1806 to the first end 1832 of the shuttle 1828. For example, the first spring 1842 can encircle a portion of an insert 1844 and a plug 1846. The plug 1846 can be a portion of the end cap 1808 or be a separate component that is connected to the end cap 1808. As shown in FIG. 18B, the insert 1844 can define a shoulder 1848 that allows the first spring 1842 to exert a force on the shuttle 1828 to cause linear motion of the shuttle 1828 as disclosed herein. The plug 1846 or the end cap 1808 also can define a shoulder 1850 to allow the first spring 1842 to rest on a stationary surface.

A second spring 1852 can mechanically couple the second end 1826 of the housing 1806 to the second end 1834 of the shuttle 1828. For example, the second spring 1852 can encircle a portion of an insert 1854 and a portion 1856 of a front end cap 1858. As shown in FIG. 18B, the insert 1854 can define a shoulder 1860 that allows the second spring 1852 to exert a force on the shuttle 1828 to cause linear motion of the shuttle 1828 as disclosed herein. The front end cap 1858 also can define a shoulder 1862 to allow the second spring 1842 to rest on a stationary surface.

The plug 1846 and the front end cap 1858 can each define an annular cavity 1864 and 1866, respectively. The first and second springs 1842 and 1852 can be located axially along a longitudinal axis of the drive rod 1816. The cavities 1864 and 1866 can allow the first spring 1842 and second spring 1852 to compress without deflection in a radial direction. By constraining the first spring 1842 and the second spring 1852 to compress in only an axial direction, energy stored in the first spring 1842 and the second spring 1852 when compressed can be released in a more efficient matter since energy is not wasted by spring movement in radial directions.

As disclosed herein, rotation of the pinion 1838 in a first direction as indicated by arrow 1868 can cause the shuttle 1828 to translate in a first direction as indicated by arrow 1870 towards the first end 1824 of the housing 1806. Rotation of the pinion 1838 in a second direction as indicated by arrow 1872 can cause the shuttle 1828 to translate the shuttle 1828 in a second direction as indicated by arrow 1874 towards the second end 1826 of the housing 1806. As disclosed herein, the shuttle 1828 can move in a linear fashion. When the shuttle 1828 is out of position so that the pinion 1838 does not mesh with the indentations 1830 of the shuttle 1828, the shuttle 1828 is freely movable by the first and second springs 1842 and 1852.

A drive rod collar 1876 can be affixed to the drive rod 1816. For example, one or more roll pins 1878 can be used to affix the drive rod collar 1876 to the drive rod 1816 as shown in FIG. 18B. Other attachment mechanisms such as set screws, welding, epoxies, etc. may be used to affix the drive rod collar 1876 to the drive rod 1816. As disclosed herein, when the shuttle 1828 travels in the first direction indicated by arrow 1870 and the pinion 1838 no longer engages the shuttle 1828, the first spring 1842 can cause the shuttle 1828 to travel in second direction as indicated by arrow 1874 and the insert 1844 can contact the drive rod collar 1876 to generate an impact force. The impact force can be transmitted via the drive rod 1816 to the chuck 1802 and a tool, such as a rasp. To generate an extraction force, the opposite can occur. For instance, the shuttle 1828 can be moved in a second direction as indicated by arrow 1874 and when the pinion 1838 no longer engages the shuttle 1828, the second spring 1852 can cause the insert 1854 to impact the drive rod collar 1876 to generate a retraction force. The retraction force can be transmitted via the drive rod 1816 to the chuck 1802 and the tool.

Figure 19A:
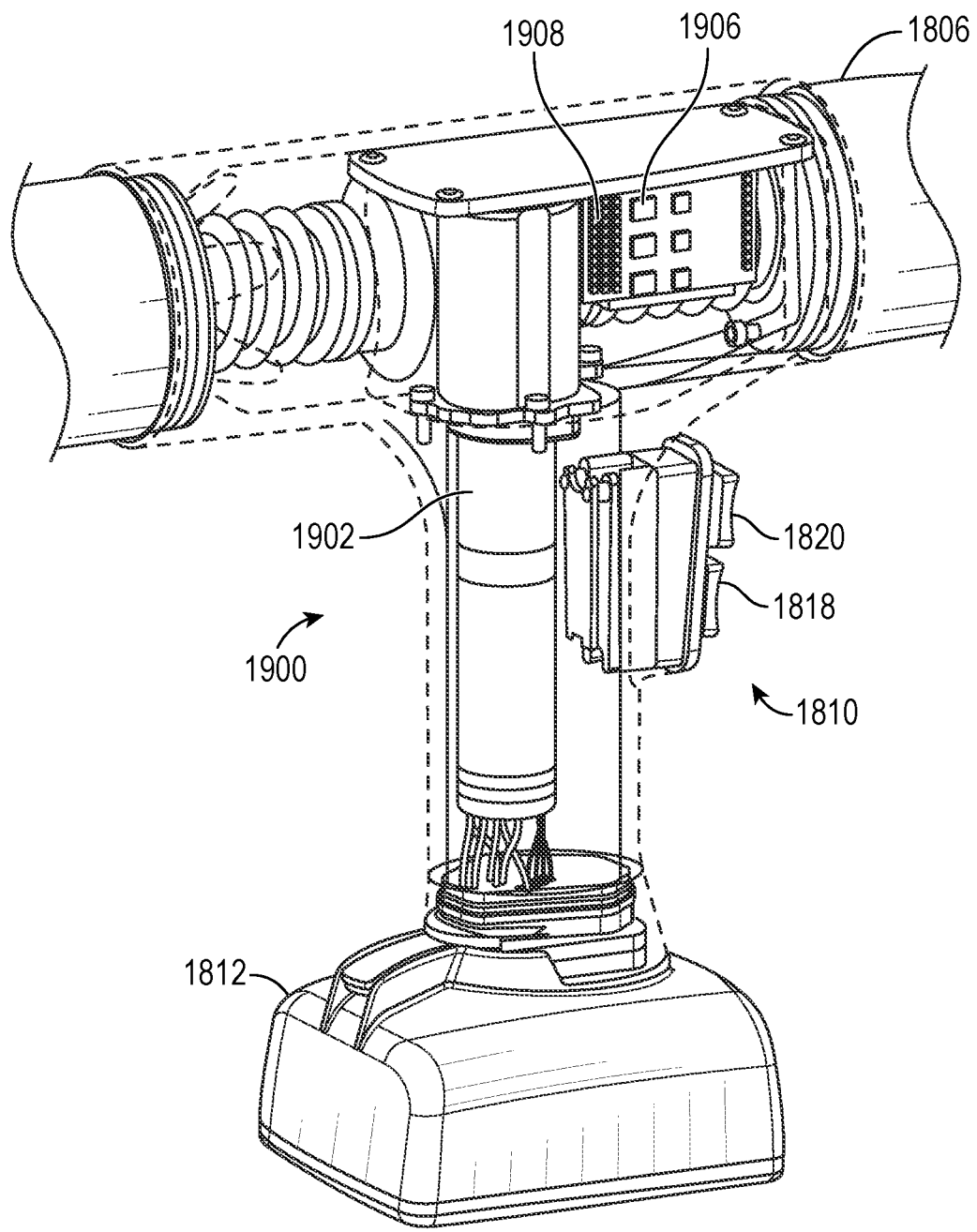
FIGS. 19A, 19B, and 19C each shows a motor pinion assembly of the bi-spring surgical impact tool of FIG. 18A consistent with at least one example of this disclosure.
Figure 19B:
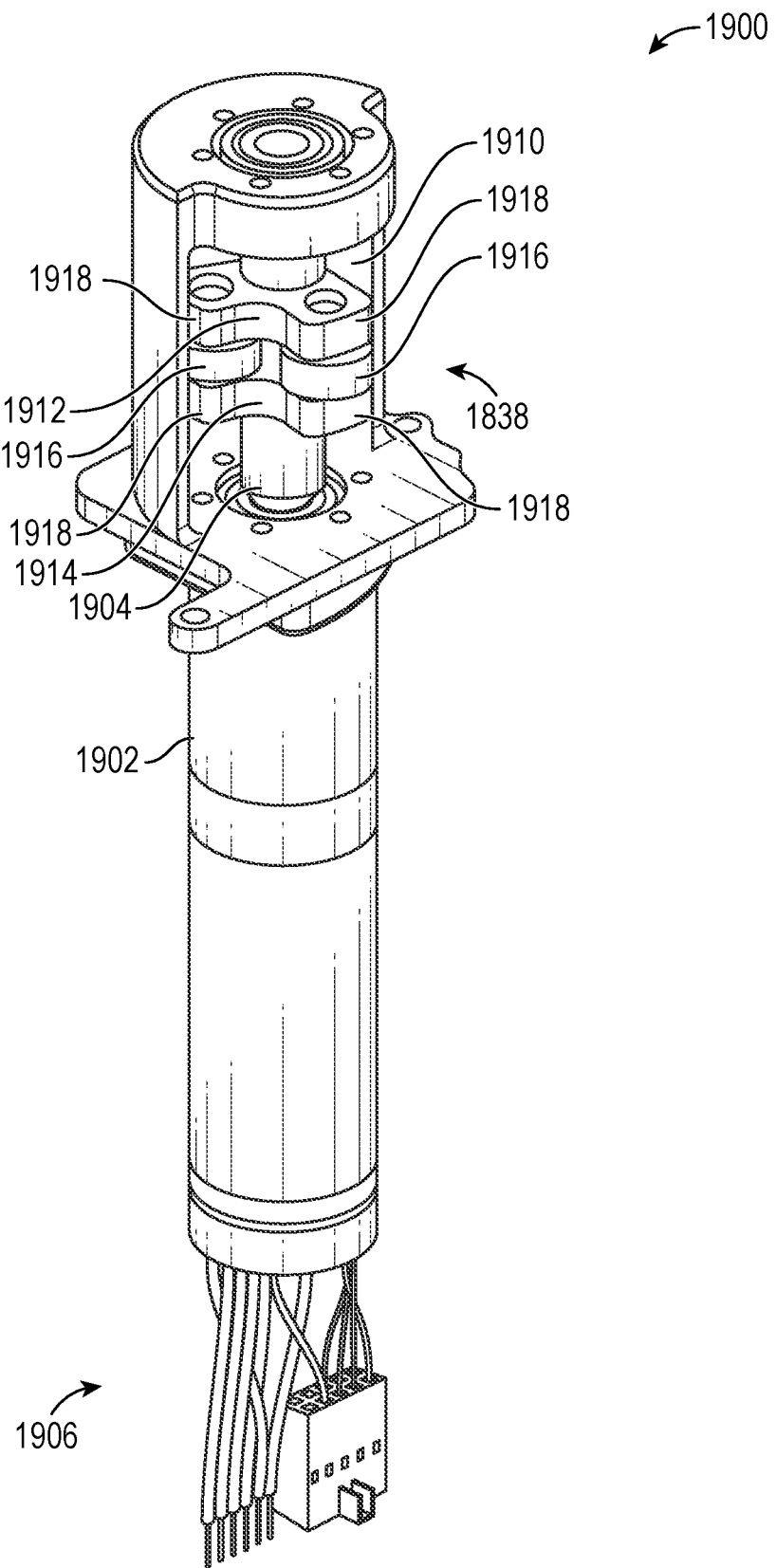
Figure 19C:
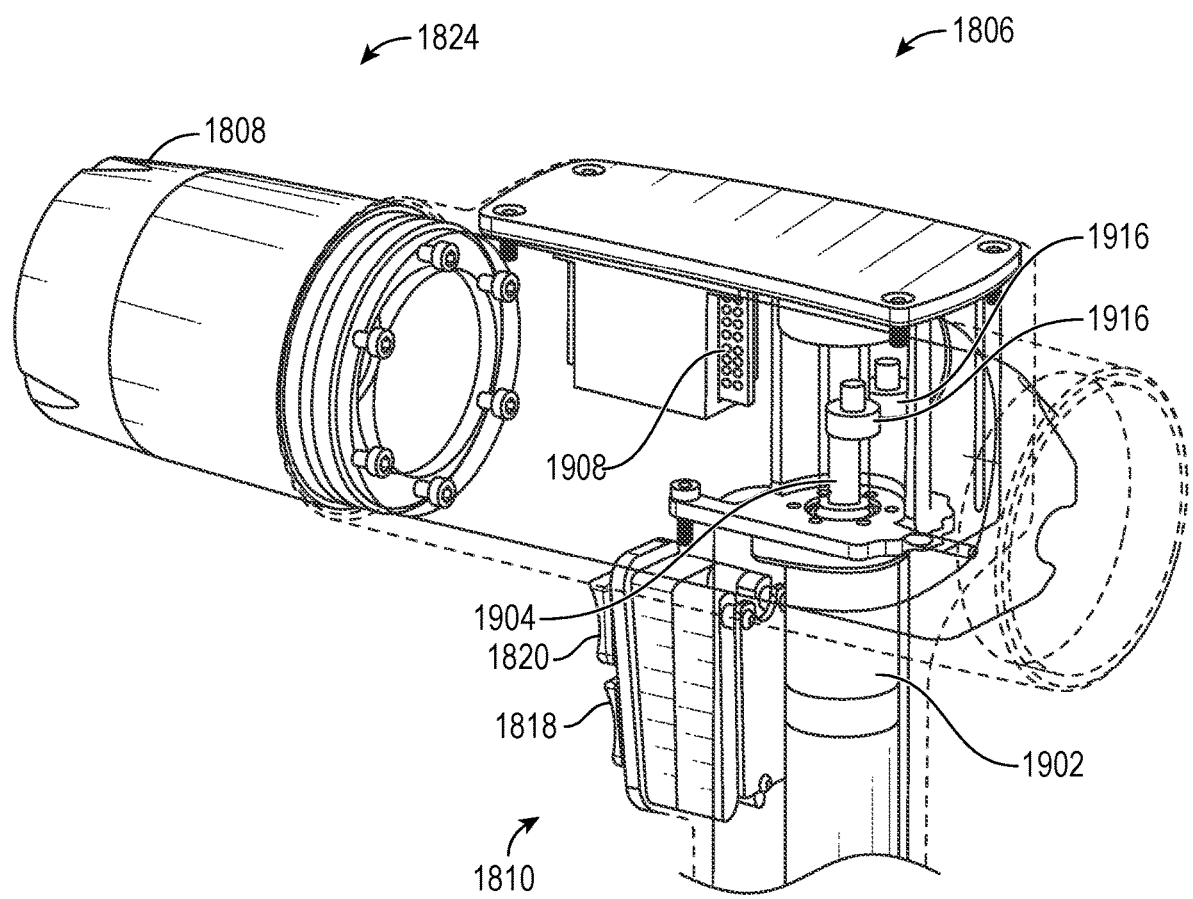

FIGS. 19A, 19B, and 19C each shows a motor pinion assembly 1900 of the bi-spring surgical impact tool 1800 of FIG. 18A consistent with at least one example of this disclosure. Motor pinion assembly 1900 can include a motor 1902 having a shaft 1904 with the pinion 1838 mounted thereto. One or more wires 1906 can be used to electrically couple the motor 1902 to the battery 1812, the trigger group 1810, a switch 1906, and a sensor 1908.

As shown in FIG. 19B, the pinion 1838 can include a pinion carriage 1910. The pinion carriage 1910 can include a first pinion plate 1912 and a second pinion plate 1914. One or more bearings 1916 can be located in between the first and second pinion plates 1912 and 1914. The bearings 1916 can form a plurality of protrusions that mesh with the indentations 1830. Non-limiting examples of the bearings 1916 include roller bearings, journal bearings, etc. The bearings 1916 can be sized to mesh with the indentations 1830 as shown in FIG. 18B so as to minimize play in between the bearings 1916 and surfaces forming the indentations 1830. Because surfaces of the bearings 1916 roll across surfaces of the indentations 1830, wear of contacting surfaces of the indentations 1830 and the bearings 1916 can be minimized without the need for grease, oil, other lubrications. A bearing sleeve can be used to allow for even radial loading on the bearing surface.

The first and second pinion plates 1912 and 1914 can each define a plurality of spokes 1918. Each of the bearings 1916 can be connected to a respective spoke 1918. While FIG. 19B shows two pinion plates, embodiments disclosed herein may use one or two pinion plates. For example, a single pinion plate, such as the first pinion plate 1912 may be used and the bearings 1916 secured to the first pinion plate 1912 via a bolt or other fastener. Also, while FIGS. 18B-19C shown the bearings 1916 attached to the pinion plates 1912 and 1914, the bearings 1916 can be attached to the shuttle 1828 and the pinion 1838 can define the indentations that mesh with the bearings 1916 attached to the shuttle 1828.

The motor 1902 can be in electrical communication with the switch 1906. The sensor 1908 can be arranged to detect a position of the shuttle 1828. For example, the sensor 1908 can be a Hall effect sensor that measures change in magnetic flux due to the movement of the drive rod 1816, which can be ferrous metal or any other material whose movement can cause a change in a magnetic field or flux. The sensor 1908 can also be in electrical communication with the switch 1906. When sensor 1908 detects that shuttle 1828 is out of position to allow indentations 1830 to mesh with the bearings 1918, or any protrusions of the pinion 1838, the switch 1906 can sever electrical communication of the motor 1902 with a power supply (i.e., battery 1812). For example, to prevent binding or other mismatching of the pinion 1838 and the shuttle 1828, the sensor 1908 can detect a position of the shuttle 1828 and halt rotation of motor the 1906 when the shuttle 1828 is not in a position to allow the spokes 1918 to mesh with the indentations 1830.

Figure 20A:
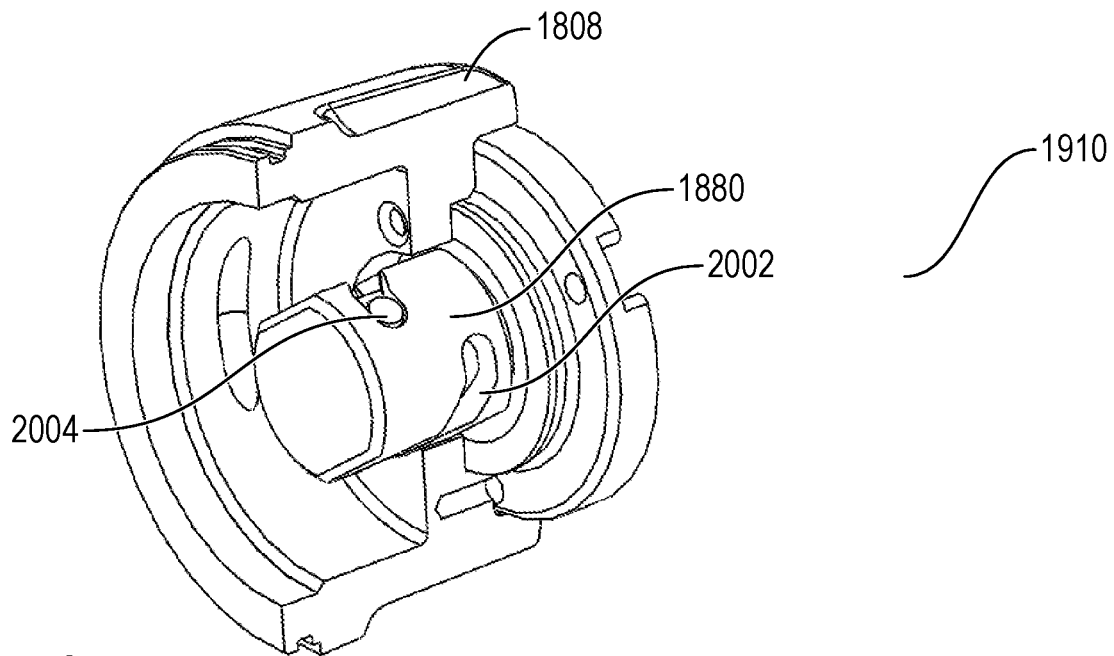
FIGS. 20A and 20B show barrel cam assembly of the bi-spring surgical impact tool of FIG. 18A consistent with at least one example of this disclosure.
Figure 20B:
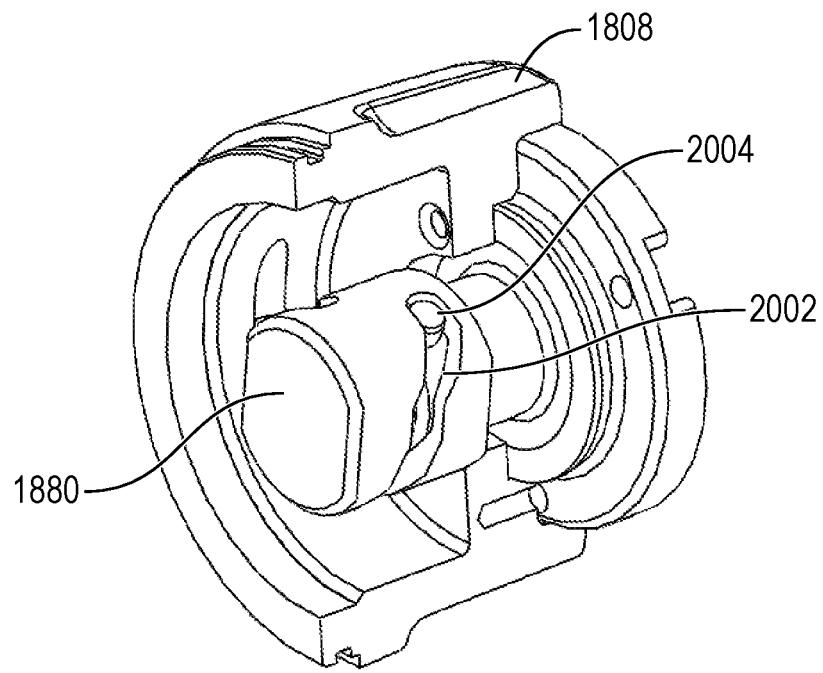

The end cap 1808 can be rotated to axially translate a barrel cam 1880 to continuously adjust the position of the drive rod 1816 and coupled drive rod collar 1876 to allow for variable magnitude impacts. As shown in FIGS. 20A and 20B, the barrel cam 1880 can include slots 2002 and pins 2004 (only one pin is visible in FIGS. 20A and 20B). The barrel cam 1880 can be rotated, such as by rotating the end cap 1808 or by using a wrench, socket, etc. Rotation of the barrel cam 1880 can cause the pins 2004 to move within the slots 2002. The movement of the pins 2004 can cause the drive rod 1816 to be repositioned in a continuous manner.

Figure 21A:
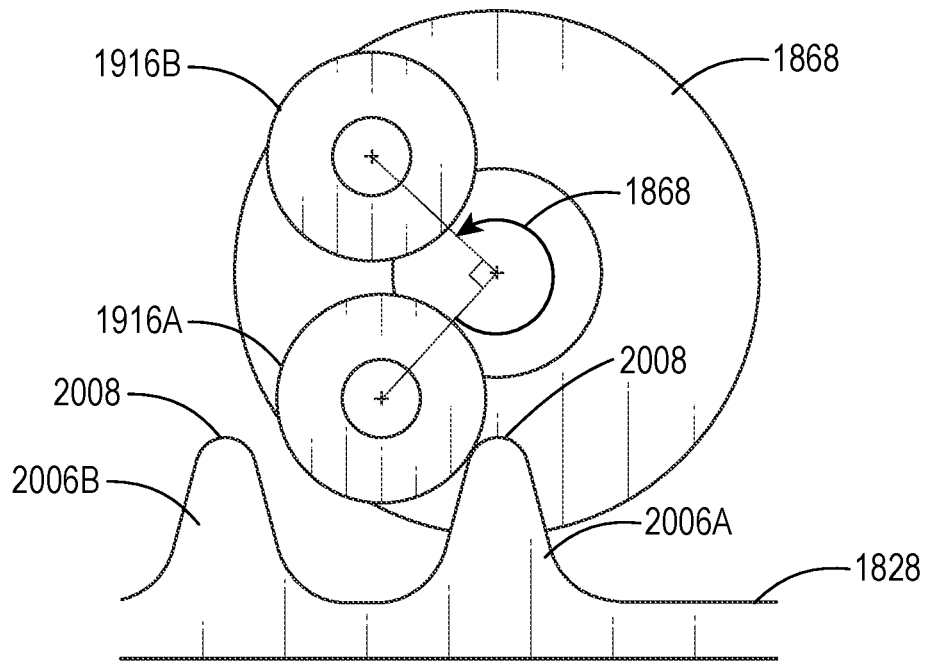
FIGS. 21A, 21B, and 21C show a shuttle and pinion assembly of the bi-spring surgical impact tool of FIG. 18A consistent with at least one example of this disclosure.
Figure 21B:
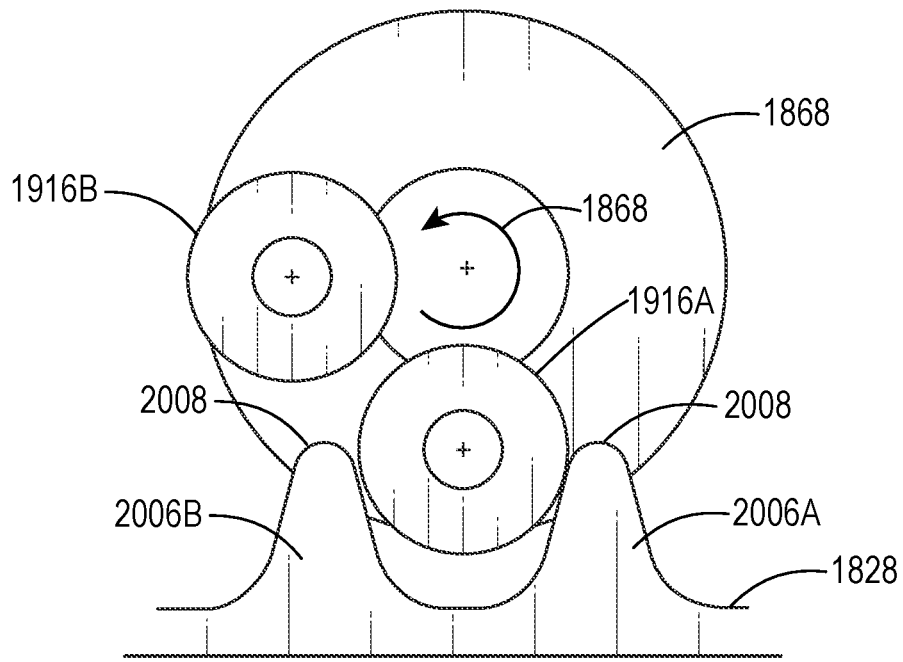
Figure 21C:
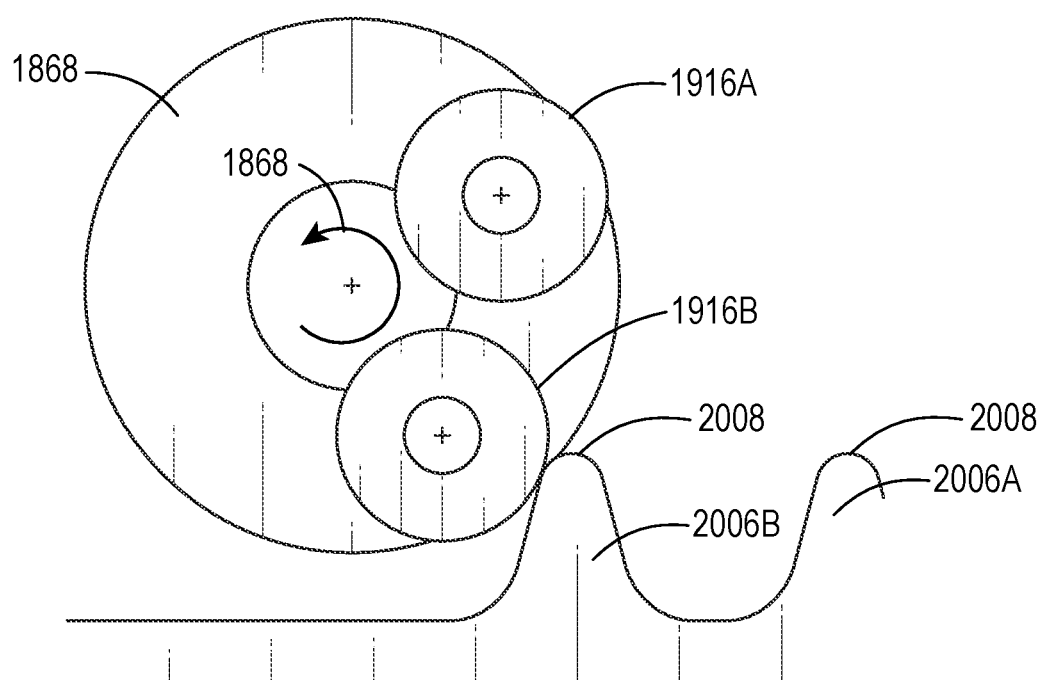

FIGS. 21A, 21B, and 21C shows the bearings 1916 (labeled individually as bearings 1916A and 1916B) and shuttle 1828 consistent with at least one example of this disclosure. As disclosed herein, the bearings 1916 and the shuttle 1828 can allow for greater forces and torque generation. The bearings 1916 and the shuttle 1828 can also reduce energy loses due to bending loads and sliding contact stresses at the point of release that may be experience in traditional rack and pinion systems. Since rolling contact between the teeth can occur even at the very last moment just before contact is lost and so there is no sliding wear.

As a non-limiting example, the bearings 1916 can have a 12.5 mm OD and installed on a pinion plate 1918, which can have a diameter of 10.4 mm. The bearings 1916 can be spaced 90° apart. The shuttle 1828 can include trapezoidal teeth 2006 (labeled individually as tooth 2006A and 2006B), which can include rounded tops 2008. For the bearing sizes stated above, the teeth 2006 can be spaced 16.5 mm apart. The initial location of the tooth center can enable in forward motion having 5 J of energy, and about 2.5 J for retraction. This also only requires the user to push forward 12 mm or pull back 12 mm to position the drive rod 1816 and chuck 1802 for impact in either direction.

As shown in FIGS. 21A, 21B, and 21C, as the pinion plate 1918 rotates in the first rotational direction as indicated by arrow 1868, bearing 1918A can contact tooth 2006A (FIG. 21A). Continued rotation of the pinion plate 1918 can cause tooth 1916B to contact tooth 2006B before bearing 1918A breaks contact with tooth 2006A, thereby reducing jerkiness and/or slippage. Continued rotation of the pinion plate 1918 will eventually cause teeth 1916 to break contact from teeth 2006 and allow the shuttle 1828 to move under the power of the first and second springs 1842 and 1852.

While FIGS. 21A, 21B, and 21C show two teeth, any number of teeth may be present. For example, FIG. 18B shows the shuttle 1828 having three teeth. As disclosed herein, the third tooth can be a "reverse tooth" that can be shorter than the two primary teeth. The shorter tooth can allow for a motor capable of 6 N-m of torque to achieve 6 J of forward energy and 3 J of retract energy.

To generate a traction or extraction force, the pinion plate 1918 can be rotated in the second direction as indicated by arrow 1872. Rotation in the second direction can cause the bearings 1918 to contact the teeth 2006 in the reverse order as described above.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A bi-spring surgical impact tool comprising:
    a housing defining a cavity having a first end and a second end;
    a shuttle located within the cavity and defining a plurality of indentations, the shuttle having a first end and a second end;
    a pinion located proximate the shuttle and having a plurality of protrusions sized to mesh with the plurality of indentations during rotation of the pinion;
    a first spring mechanically coupling the first end of the housing to the first end of the shuttle; and
    a second spring mechanically coupling the second end of the housing to the second end of the shuttle,
    wherein rotation of the pinion in a first rotational direction translates the shuttle in a first linear direction towards the first end of the housing and rotation of the pinion in a second rotational direction translates the shuttle in a second linear direction towards the second end of the housing.

2. The bi-spring surgical impact tool of claim 1, wherein the pinion comprises:
    a pinion carriage; and
    a plurality of bearings that form the plurality of protrusions.

3. The bi-spring surgical impact tool of claim 2, wherein the pinion carriage comprises a pinion plate defining a plurality of spokes, each of the plurality of bearings connected to a respective spoke of the pinion plate.

4. The bi-spring surgical impact tool of claim 2, wherein the pinion carriage comprises first and second pinion plates defining a plurality of spokes, each of the plurality of bearings located in between respective spokes of the first and second pinion plates.

5. The bi-spring surgical impact tool of claim 1, further comprising a drive rod oriented along an axis of the housing extending from the first end of the housing to the second end of the housing, the shuttle translatable along the drive rod, the shuttle and drive rod movable in the first and second linear directions along the axis of the housing.

6. The bi-spring surgical impact tool of claim 5, wherein the first and second springs are located axially along a longitudinal axis of the drive rod.

7. The bi-spring surgical impact tool of claim 5, further comprising:
    a drive rod collar affixed to the drive rod; and
    an insert coupled to the first spring and arranged to impact the drive rod collar upon disengagement of the plurality of protrusions from the plurality of the indentations.

8. The bi-spring surgical impact tool of claim 1, further comprising:
    a motor;
    a switch; and
    a sensor arranged to detect a position of the shuttle and in electrical communication with the switch,
    wherein when the shuttle is out of position to allow the plurality of indentations of the shuttle to mesh with the plurality of the protrusions of the pinion, the switch severs electrical communication of the motor to a power supply.

9. The bi-spring surgical impact tool of claim 6, wherein the sensor is a Hall effect sensor.

10. The bi-spring surgical impact tool of claim 1, further comprising a chuck mechanically coupled to the shuttle.

11. A bi-spring surgical impact tool comprising:
a housing defining a cavity having a housing axis that extends from a first end of the housing to a second end of the housing;
a drive rod having a drive rod axis oriented parallel to the housing axis;
a drive rod collar connected to the drive rod;
a shuttle translatable along the drive rod and having a plurality of shuttle teeth;
a pinion located proximate the shuttle and having a plurality of pinion teeth sized to mesh with the plurality of shuttle teeth;
a first spring mechanically coupling the first end of the housing to the first end of the shuttle, the first spring located coaxially with the drive rod; and
a second spring mechanically coupling the second end of the housing to the second end of the shuttle, the second spring located coaxially with the drive rod,
wherein rotation of the pinion in a first rotational direction translates the shuttle in a first direction towards the first end of the housing and rotation of the pinion in a second rotational direction translates the shuttle in a second direction towards the second end of the housing,
wherein when the shuttle is out of position to allow the plurality of shuttle teeth to mesh with the plurality of pinion teeth, the shuttle is movable by the first and second springs.

12. The bi-spring surgical impact tool of claim 11, wherein the pinion comprises:
a pinion carriage; and
a plurality of bearings that form the teeth.

13. The bi-spring surgical impact tool of claim 12, wherein the pinion carriage comprises a pinion plate defining a plurality of spokes, each of the plurality of bearings connected to a respective spoke of the pinion plate.

14. The bi-spring surgical impact tool of claim 12, wherein the pinion carriage comprises first and second pinion plates defining a plurality of spokes, each of the plurality of bearings located in between respective spokes of the first and second pinion plates.

15. The bi-spring surgical impact tool of claim 11, further comprising:
a motor;
a switch; and
a sensor arranged to detect a position of the shuttle and in electrical communication with the switch,
wherein when the shuttle is out of position to allow the plurality of shuttle teeth to mesh with the plurality of pinion teeth, the switch severs electrical communication of the motor to a power supply.

16. A bi-spring surgical impact tool comprising:
a housing defining a cavity having a housing axis that extends from a first end of the housing to a second end of the housing;
a drive rod having a drive rod axis oriented parallel to the housing axis;
a drive rod collar connected to the drive rod;
a shuttle translatable along the drive rod and having a plurality of shuttle teeth;
a pinion located proximate the shuttle and having a plurality of pinion teeth sized to mesh with the plurality of shuttle teeth;
a first spring mechanically coupled to the first end of the housing, the first spring located coaxially with the drive rod;
a first insert coupled to the shuttle and the first spring, the first insert defining a first insert shoulder arranged to contact the drive rod collar and drive the drive rod in a first linear direction under a first force generated by the first spring;
a second spring mechanically coupled to the second end of the housing, the second spring located coaxially with the drive rod; and
a second insert coupled to the shuttle and the second spring, the second insert defining a second insert shoulder arranged to contact the drive rod collar and drive the drive rod in a second linear direction under a second force generated by the second spring,
wherein rotation of the pinion in a first rotational direction translates the shuttle in the second linear direction and rotation of the pinion in a second rotational direction translates the shuttle in the first linear direction,
wherein when the shuttle is out of position to allow the plurality of shuttle teeth to mesh with the plurality of pinion teeth, the shuttle is movable by the first and second springs in the first and second directions.

17. The bi-spring surgical impact tool of claim 16, wherein the pinion comprises: a pinion carriage; and a plurality of bearings that form the plurality of pinion teeth.

18. The bi-spring surgical impact tool of claim 17, wherein the pinion carriage comprises a pinion plate defining a plurality of spokes, each of the plurality of bearings connected to a respective spoke of the pinion plate.

19. The bi-spring surgical impact tool of claim 17, wherein the pinion carriage comprises first and second pinion plates defining a plurality of spokes, each of the plurality of bearings located in between respective spokes of the first and second pinion plates.

20. The bi-spring surgical impact tool of claim 16, further comprising:
a motor;
a switch; and
a sensor arranged to detect a position of the shuttle and in electrical communication with the switch,
wherein when the shuttle is out of position to allow the plurality of shuttle teeth to mesh with the plurality of pinion teeth, the switch severs electrical communication of the motor to a power supply.

* * * * *